US005617848A

United States Patent [19]

Cochran

[11] Patent Number: 5,617,848

[45] Date of Patent: Apr. 8, 1997

[54] ADVANCED DIVE COMPUTER THAT CALCULATES AND DISPLAYS THE USER'S BREATHING PARAMETER AND WATER SALINITY

[76] Inventor: Michael J. Cochran, 2505 Evane Dr., Plano, Tex. 75075

[21] Appl. No.: 514,363

[22] Filed: Aug. 11, 1995

Related U.S. Application Data

[63] Continuation of Ser. No. 154,022, Nov. 17, 1993, abandoned.

[51] Int. Cl.[6] .............................. A62B 7/00; A62B 9/00; A61M 16/00; G08B 3/00

[52] U.S. Cl. .............................. 128/205.23; 128/202.22; 128/205.22; 128/201.27

[58] Field of Search ......................... 128/200.24, 201.27, 128/201.28, 202.22, 204.18, 204.23, 204.22, 204.26, 205.23, 205.24, 205.22; 364/413.3, 413.31, 558, 565, 569; 367/131, 134; 340/850; 73/865.1

[56] References Cited

U.S. PATENT DOCUMENTS

| | | | |
|---|---|---|---|
| 4,192,001 | 3/1980 | Villa | 364/413.31 |
| 4,563,758 | 1/1986 | Paternostro | 367/132 |
| 4,586,136 | 4/1986 | Lewis | 364/413.31 |
| 4,658,358 | 4/1987 | Leach et al. | 364/413.31 |
| 4,783,772 | 11/1988 | Umemoto et al. | 368/11 |
| 4,835,716 | 5/1989 | Tamaki et al. | 364/558 |
| 4,882,678 | 11/1989 | Hollis et al. | 364/413.31 |
| 4,949,072 | 8/1990 | Comerford et al. | 340/525 |
| 4,970,897 | 11/1990 | Budinger | 73/432.1 |
| 4,999,606 | 3/1991 | Comerford et al. | 340/525 |
| 5,016,483 | 5/1991 | Budinzer | 73/865.1 |
| 5,031,160 | 7/1991 | Koizumi et al. | 368/10 |
| 5,033,818 | 7/1991 | Barr | 359/630 |
| 5,103,685 | 4/1992 | Wright | 73/865.1 |
| 5,148,376 | 9/1992 | Sato | 364/558 |
| 5,189,646 | 2/1993 | Sako et al. | 368/10 |

OTHER PUBLICATIONS

*The International Dictionary of Physics and Electronics*, Copyright 1956 by D. Van Nostrandt Company, pp. 703–704.

*Primary Examiner*—Kimberly L. Asher
*Attorney, Agent, or Firm*—Jones, Day, Reavis & Pogue

[57] ABSTRACT

A dive computer for use by a user of a self-contained underwater breathing apparatus that calculates and displays the user's breathing parameter, which is indicative of the rate at which air pressure in the user's compressed-air tank is decreasing normalized with respect to the user's depth. The dive computer measures the salinity of the water and bases the depth calculation on whether the diver is in fresh or sea water. The dive computer can be actuated by tapping.

34 Claims, 11 Drawing Sheets

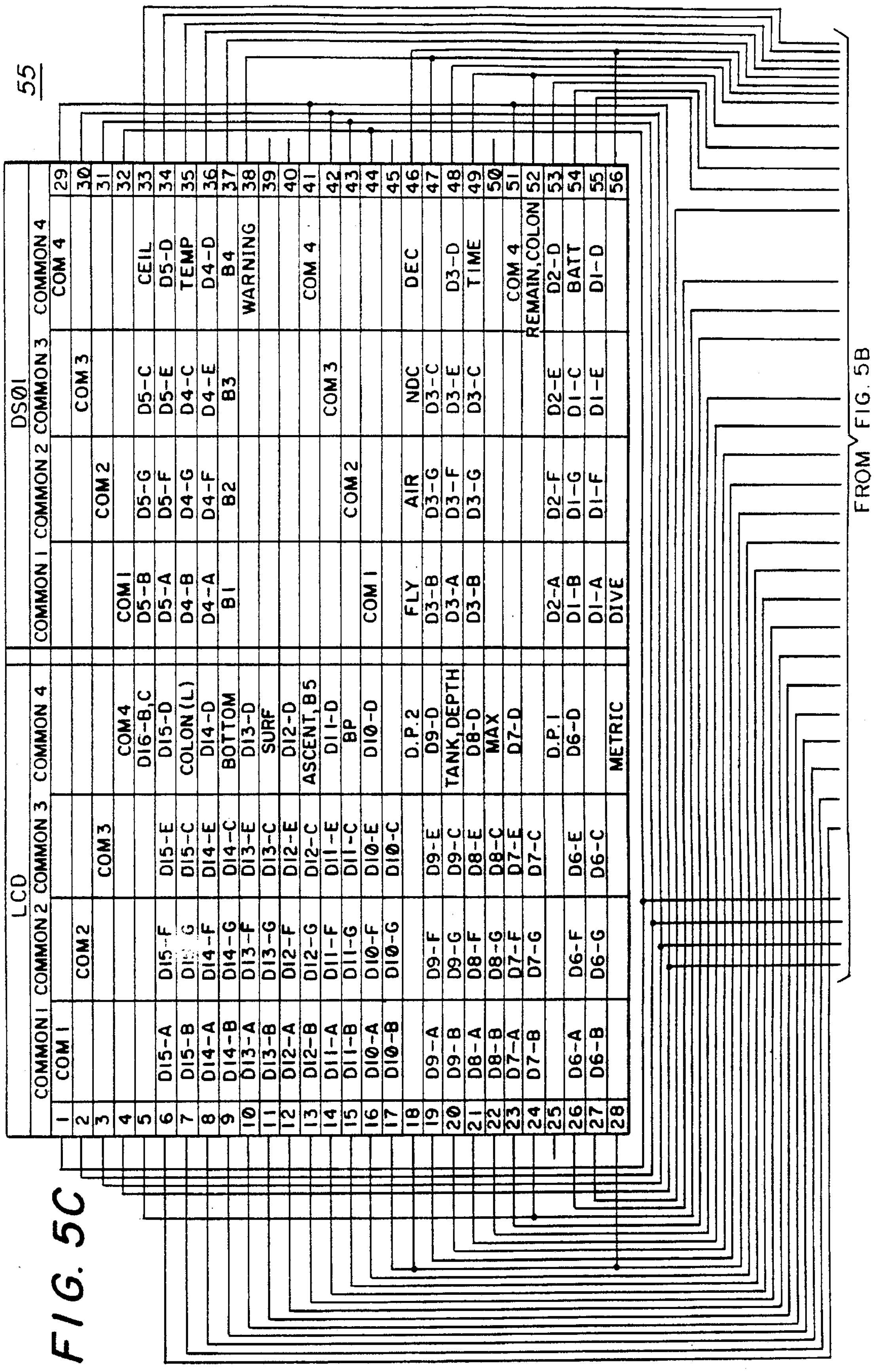

| | LCD COMMON 1 | LCD COMMON 2 | LCD COMMON 3 | LCD COMMON 4 | | DS01 COMMON 1 | DS01 COMMON 2 | DS01 COMMON 3 | DS01 COMMON 4 |
|---|---|---|---|---|---|---|---|---|---|
| 1 | COM 1 | | | | 29 | | | | COM 4 |
| 2 | | COM 2 | | | 30 | | | COM 3 | |
| 3 | | | COM 3 | | 31 | | COM 2 | | |
| 4 | | | | COM 4 | 32 | COM 1 | | | |
| 5 | | | | D16-B,C | 33 | D5-B | D5-G | D5-C | CEIL |
| 6 | D15-A | D15-F | D15-E | D15-D | 34 | D5-A | D5-F | D5-E | D5-D |
| 7 | D15-B | D15-G | D15-C | COLON (L) | 35 | D4-B | D4-G | D4-C | TEMP |
| 8 | D14-A | D14-F | D14-E | D14-D | 36 | D4-A | D4-F | D4-E | D4-D |
| 9 | D14-B | D14-G | D14-C | BOTTOM | 37 | B1 | B2 | B3 | B4 |
| 10 | D13-A | D13-F | D13-E | D13-D | 38 | | | | WARNING |
| 11 | D13-B | D13-G | D13-C | SURF | 39 | | | | |
| 12 | D12-A | D12-F | D12-E | D12-D | 40 | | | | |
| 13 | D12-B | D12-G | D12-C | ASCENT, B5 | 41 | | | | COM 4 |
| 14 | D11-A | D11-F | D11-E | D11-D | 42 | | | COM 3 | |
| 15 | D11-B | D11-G | D11-C | BP | 43 | | COM 2 | | |
| 16 | D10-A | D10-F | D10-E | D10-D | 44 | COM 1 | | | |
| 17 | D10-B | D10-G | D10-C | | 45 | | | | |
| 18 | | | | D.P.2 | 46 | FLY | AIR | NDC | DEC |
| 19 | D9-A | D9-F | D9-E | D9-D | 47 | D3-B | D3-G | D3-C | |
| 20 | D9-B | D9-G | D9-C | TANK, DEPTH | 48 | D3-A | D3-F | D3-E | D3-D |
| 21 | D8-A | D8-F | D8-E | D8-D | 49 | D3-B | D3-G | D3-C | TIME |
| 22 | D8-B | D8-G | D8-C | MAX | 50 | | | | |
| 23 | D7-A | D7-F | D7-E | D7-D | 51 | | | | COM 4 |
| 24 | D7-B | D7-G | D7-C | | 52 | | | | REMAIN, COLON |
| 25 | | | | D.P.1 | 53 | D2-A | D2-F | D2-E | D2-D |
| 26 | D6-A | D6-F | D6-E | D6-D | 54 | D1-B | D1-G | D1-C | BATT |
| 27 | D6-B | D6-G | D6-C | | 55 | D1-A | D1-F | D1-E | D1-D |
| 28 | | | | METRIC | 56 | DIVE | | | |

FIG. 5C

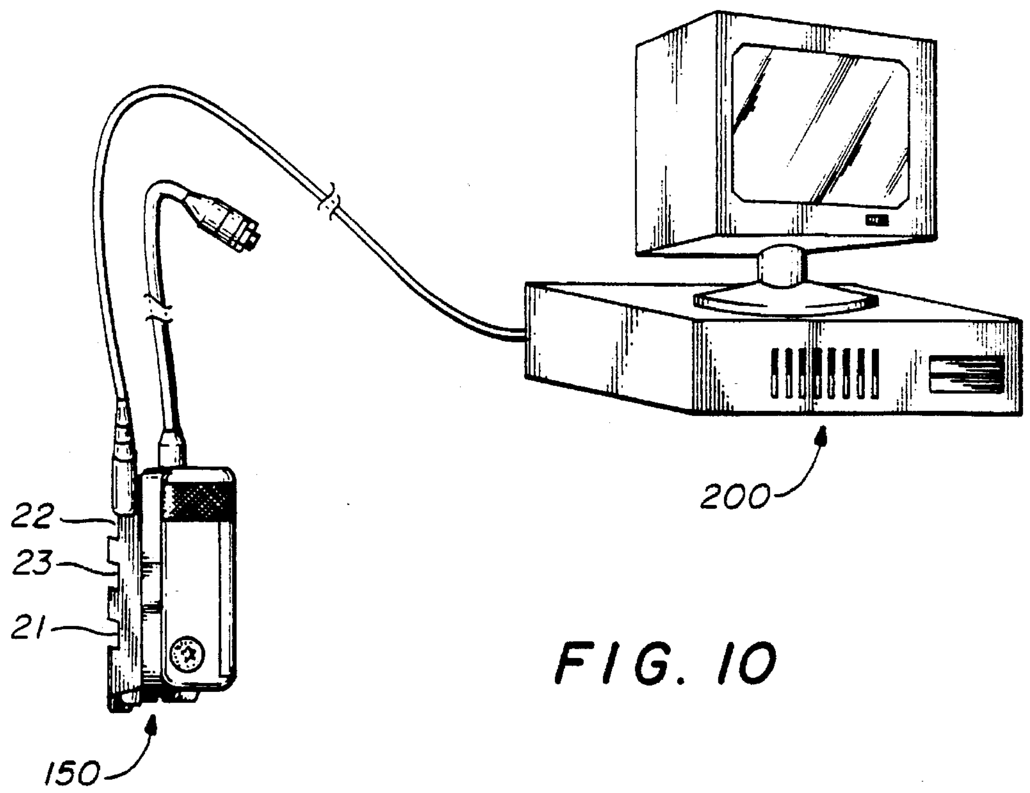
FIG. 10
FIG. 11
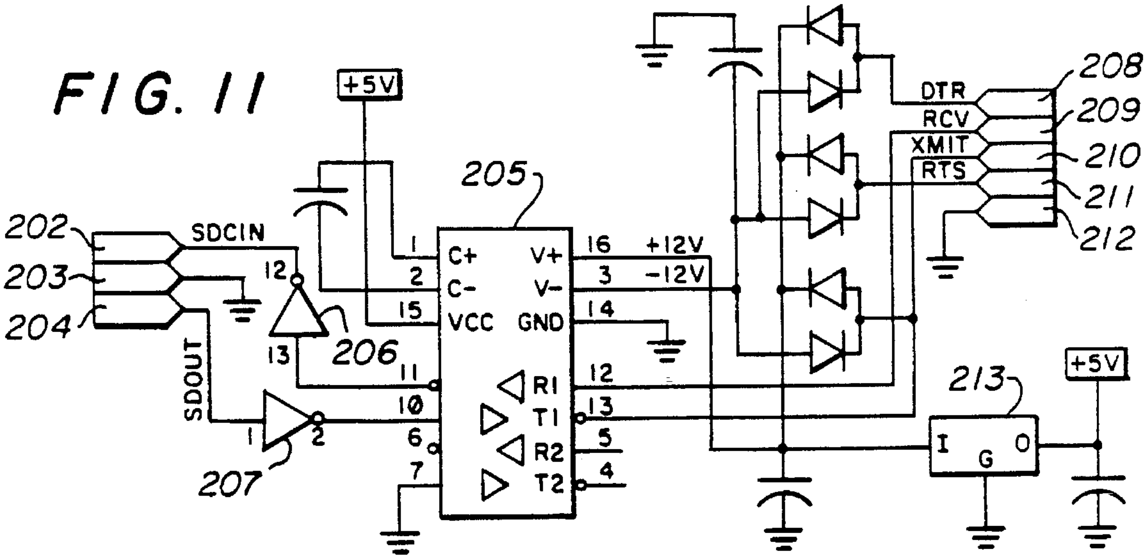

ADVANCED DIVE COMPUTER THAT CALCULATES AND DISPLAYS THE USER'S BREATHING PARAMETER AND WATER SALINITY

This is a continuation of application Ser. No. 08/154,022 filed on Nov. 17, 1993; now abandoned.

BACKGROUND OF THE INVENTION

1. Field of the Invention

This invention relates generally to a dive computer for use by a user of a self-contained underwater breathing apparatus (SCUBA), and particularly to an advanced dive computer that calculates and displays the user's breathing parameter, which is indicative of the rate at which air pressure is decreasing in the user's compressed-air tank normalized with respect to the depth of the user and the salinity of the water.

2. Description of Related Art

Although sport diving can be fun, exciting and physically demanding, there are a variety of potential hazards that must be avoided. In particular, sport diving can be exceedingly dangerous if the diver becomes disoriented or light-headed. Thus, it is desirable for a diver to be able to monitor the rate at which he is consuming air. This task is complicated because the amount of air a diver actually breathes varies with depth even though the diver's breathing rate remains unchanged. For example, if a diver consumes 20 psi per minute while breathing at a normal rate on the surface, he will consume 80 psi per minute if breathing at the same rate at a depth of 99 feet. Thus, for a diver to easily monitor his breathing rate, it is essential that the rate at which he is consuming air be normalized to eliminate the variable of depth.

There are several dive computers available today that display conventional dive parameters such as the amount of air pressure remaining in the user's compressed-air tank, the depth of the user and in some instances the temperature of the surrounding water. Although display of these dive parameters provides the user with a "snap-shot" of his current conditions, they do not allow the user to monitor his rate of air consumption.

Accordingly, an object of the present invention is to provide a dive computer that calculates and displays the user's breathing parameter, which is indicative of the rate at which air pressure in the user's compressed-air tank is decreasing normalized with respect to the depth of the user. Another object of the present invention is to provide a method for calculating the user's breathing parameter.

A diver's breathing parameter is essentially a measure of his breathing efficiency. The more a person dives, the more efficient his breathing should become. Thus, another object of the present invention is to provide a dive computer that stores the diver's breathing parameter in memory for later retrieval so that a diver can track his progress from dive to dive.

Since a diver will not normally stop breathing or suddenly triple his breathing rate, his breathing parameter will not normally go to either an extremely low or high level, and will not normally undergo rapid changes. Thus, a diver's breathing parameter provides an indication of whether the diver is unduly stressed or in trouble and an indication of whether the diver's equipment, including the dive computer itself, is operating correctly. Accordingly, another object of the present invention is to provide a dive computer that provides a visible warning and sounds an audible alarm when the diver's breathing parameter either undergoes a rapid change or reaches an extremely low or high level.

SUMMARY OF THE INVENTION

These and other objects and advantages of the invention are accomplished by a dive computer for use by a user of a self contained underwater breathing apparatus. The dive computer includes a high pressure transducer for sensing air pressure in the user's compressed-air tank, a low pressure transducer for sensing ambient pressure, a microcomputer coupled to each these transducers for calculating the user's breathing parameter and a display coupled to the microcomputer for displaying the user's breathing parameter. In accordance with the present invention, the transducers and microcomputer are included in a tank unit that is physically separate from the display, which is contained in a display unit. The invention may alternatively be assembled with the high pressure transducer in the tank unit and the low pressure transducer, the microcomputer and the display located in the display unit. Moreover, the invention may be assembled as a single unit.

The invention may also include an alarm circuit that sounds an audible alarm whenever the user's breathing parameter either undergoes a rapid change or reaches an extremely high or low level.

The present invention provides a method for calculating a diver's breathing parameter, which is indicative of the normalized rate at which air pressure in the diver's compressed-air tank is decreasing. This method includes the steps of measuring air pressure in the user's compressed-air tank and calculating the rate at which air pressure in the user's compressed-air tank is decreasing. This method also includes measuring ambient pressure and calculating the depth of the user for each time interval for which air pressure in the user's compressed-air tank is measured. In the preferred form, each of these measurements and calculations takes place once each second, From this information the user's breathing parameter can be determined in accordance with the present invention by calculating the normalized rate at which air pressure in the user's compressed-air tank is decreasing. This is accomplished by dividing the calculated rate at which air pressure in the compressed-air tank is decreasing by the depth of the user. Specifically the user's instantaneous breathing parameter may be calculated according to the following:

$$I.B.P. = \frac{(\Delta \text{ tank pressure})}{(\text{depth in feet}/33 \text{ feet}) + 1}$$

In the preferred form the user's instantaneous breathing parameter is averaged over a 64 second time span and then multiplied by 60 so that the actual breathing parameter displayed to the user is indicative of the rate at which air pressure in user's compressed-air tank is decreasing in psi per minute, normalized for depth, The user's actual breathing parameter is also stored in memory for later retrieval by the user.

BRIEF DESCRIPTION OF THE DRAWINGS

The novel and useful features of the invention are set forth in the claims. The invention itself, as well as specific features and advantages of the invention may be best understood by reference to the detailed description of the preferred embodiment that follows, when read in conjunction with the accompanying drawing.

FIGS. 5A through 5C form is an electrical schematic of the display unit of the dive computer.

FIG. 10 illustrates a personal computer, connected to the dive computer shown in FIG. 1 through a data probe.

FIG. 11 is an electrical schematic of the data probe illustrated in FIG. 10.

DESCRIPTION OF THE PREFERRED EMBODIMENT

Figure 1:
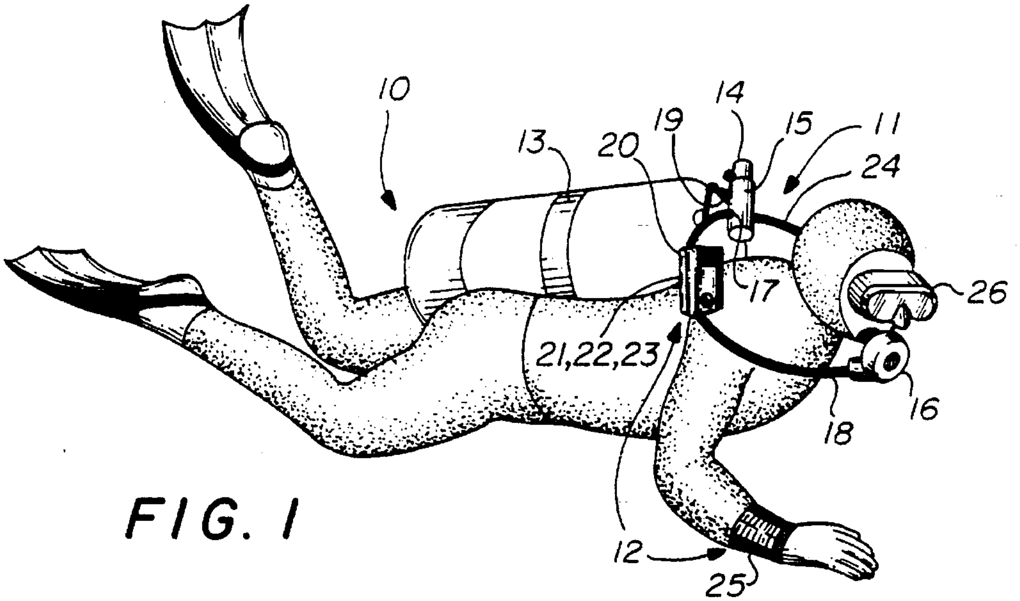
FIG. 1 illustrates a conventional self-contained underwater breathing apparatus (SCUBA), and a dive computer constructed in accordance with the preferred embodiment of the present invention.

FIG. 1 illustrates a diver 10 using a conventional self-contained underwater breathing apparatus (SCUBA) 11, and a dive computer 12 constructed in accordance with the present invention.

A conventional self-contained underwater breathing apparatus 11 typically includes a compressed-air tank 13, to which a high pressure tank valve 14 and a first stage regulator 15 are connected. A conventional self-contained breathing apparatus also includes a second stage regulator 16 connected to the low pressure port 17 of first stage regulator 15 by a low pressure hose 18. First stage regulator 15 also has a high pressure port 19. The high pressure tank valve 14 has a control knob or handle that allows the controlled release of the air in compressed-air tank 13 by an O-ring sealed high pressure outlet port to first stage regulator 15. First stage regulator 15 has a high pressure inlet port that is typically connected to the high pressure outlet port of valve 14 by a yoke screw. In operation, first stage regulator 15 supplies air from compressed-air tank 13 to second stage regulator 16 via low pressure hose 18 at a relatively constant, intermediate pressure, substantially independent of the pressure in compressed-air tank 13.

In the preferred form, dive computer 12 consists of a tank unit 20 and a display unit 25. The tank unit connects to the high pressure port 19 of the first stage regulator 15 and may be physically attached by metal clasps 21 through 23 to any available low pressure hose, such as low pressure hose 18 or low pressure hose 24, which goes to the user's buoyancy compensator. The display unit 25 is adapted to be attached to the user so that it is readily visible. It may be worn by the user like a wrist watch or attached to the user's buoyancy compensator. Alternatively, display unit 25 may be integrated into the user's mask 26 so that dive parameter information can be displayed in the dive's field of view, thus, providing a complete "hands free" working environment.

As seen in FIG. 1, in the preferred form, the display unit is physically separate from the tank unit. Many of the useful and unique features of dive computer 12 may, however, be incorporated into a dive computer that consists of a single unit.

The Dive Computer 12

Figure 2:
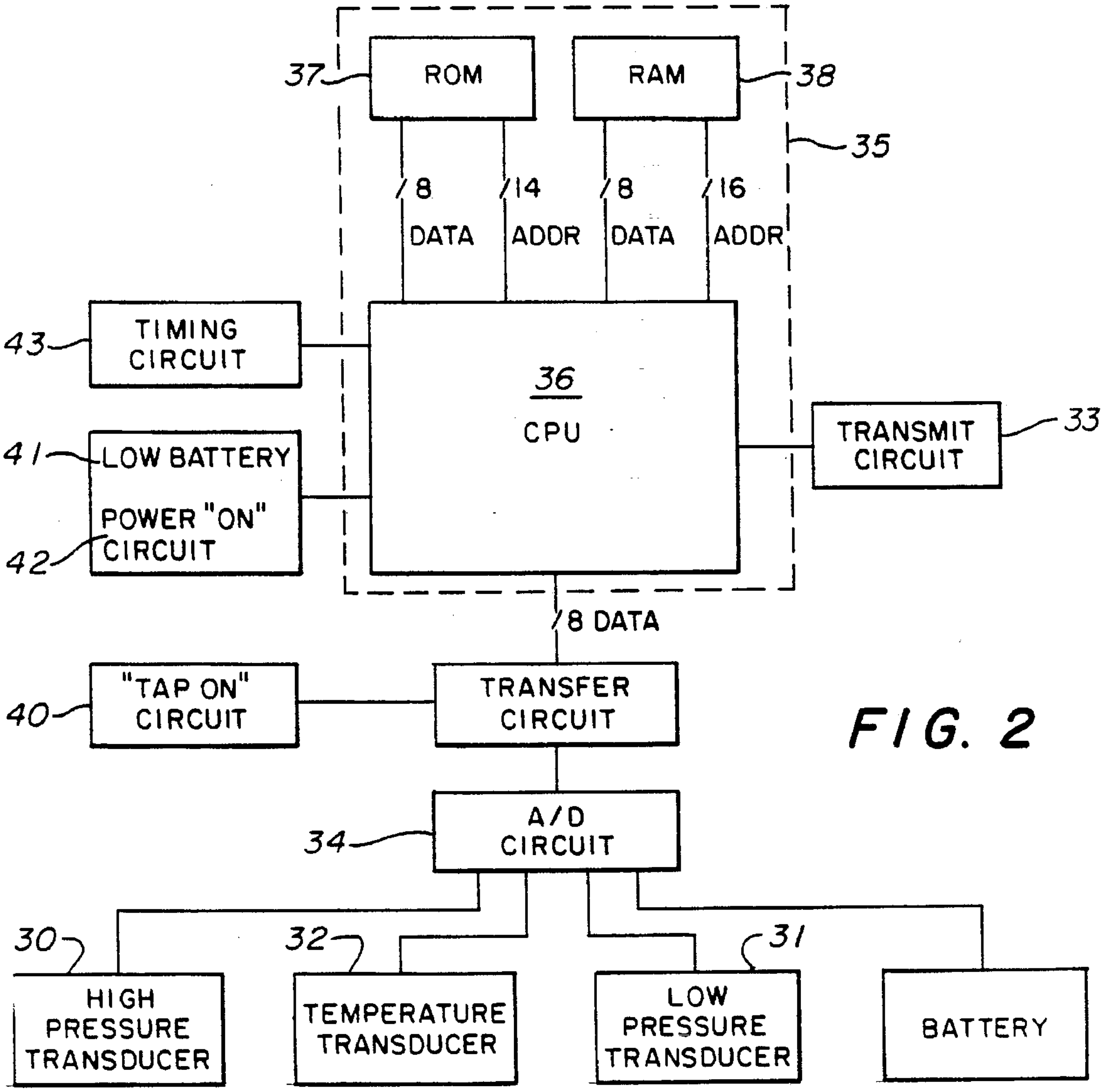
FIG. 2 is a block diagram that illustrates the functional elements of the tank unit of the dive computer.

FIG. 2 is a block diagram that illustrates the functional elements of the dive computer tank unit 20 shown in FIG. 1. Tank unit 20 includes devices for measuring various dive parameters including at least a high-pressure transducer 30 for measuring the air pressure in compressed-air tank 13, a low-pressure transducer 31 for measuring ambient pressure and a temperature sensor 32 for measuring ambient temperature. Tank unit 20 also includes a transmitter 33 for transmitting dive parameter information to display unit 25, so that there is no physical connection between tank unit 20 and display unit 25. In the preferred form, tank unit 20 also includes an A/D converter 34 for converting analog measurements to digital information and a microcomputer 35 to collect, calculate and store various dive parameters including the air pressure in compressed-air tank 13, the depth of the user, the length of time the user can safely remain at that depth and the temperature of the surrounding water. In the preferred form, microcomputer 35 includes a microprocessor 36, a read only memory (ROM) 37 and a random access memory (RAM) 38. Alternatively, microcomputer 35 may include a flash memory device or any other suitable form of memory. Microcomputer 35 may also be consolidated into a single-chip device, such as microcontroller. In the preferred form, tank unit 20 also includes an electrically alterable read only memory (EAROM) 39 for storing the operational parameters of the dive computer; a "tap on" circuit 40 for turning the tank unit on; a low-battery detect circuit 41 and power-on circuit 42 to ensure proper operation of the tank unit; and a timing circuit 43.

Figure 3:
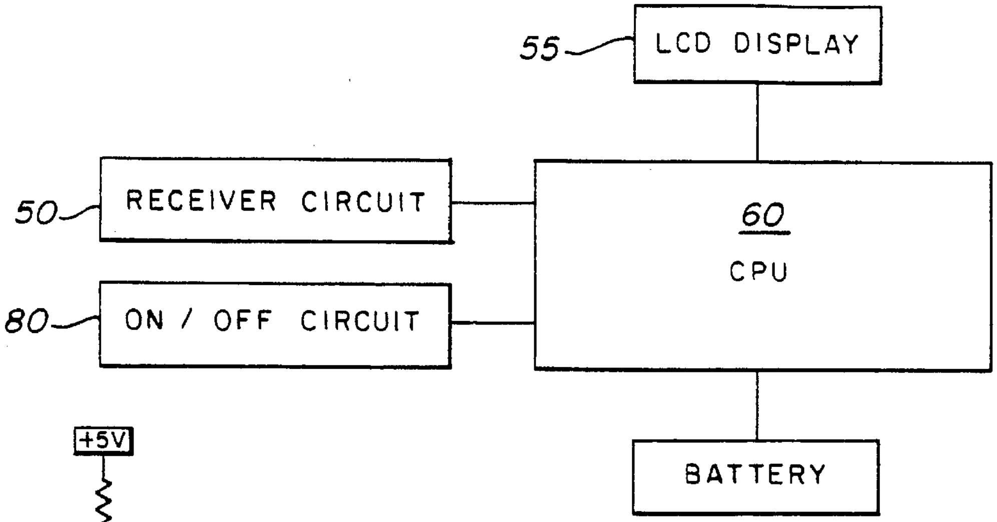
FIG. 3 is a block diagram that illustrates the functional elements of the display unit of the dive computer.
Figure 4A:
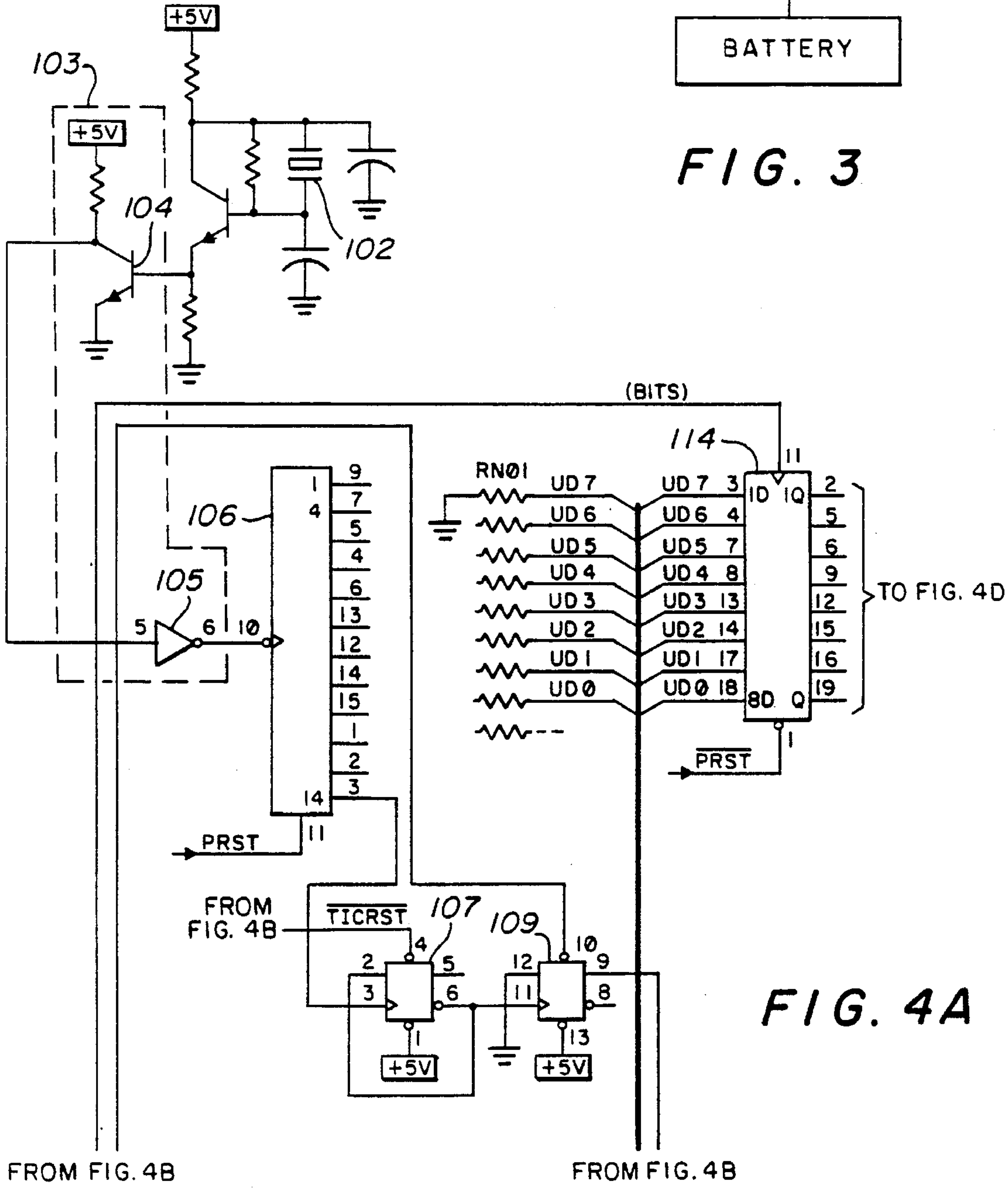
FIGS. 4A through 4F form an electrical schematic of the tank unit of the dive computer.
Figure 4B:
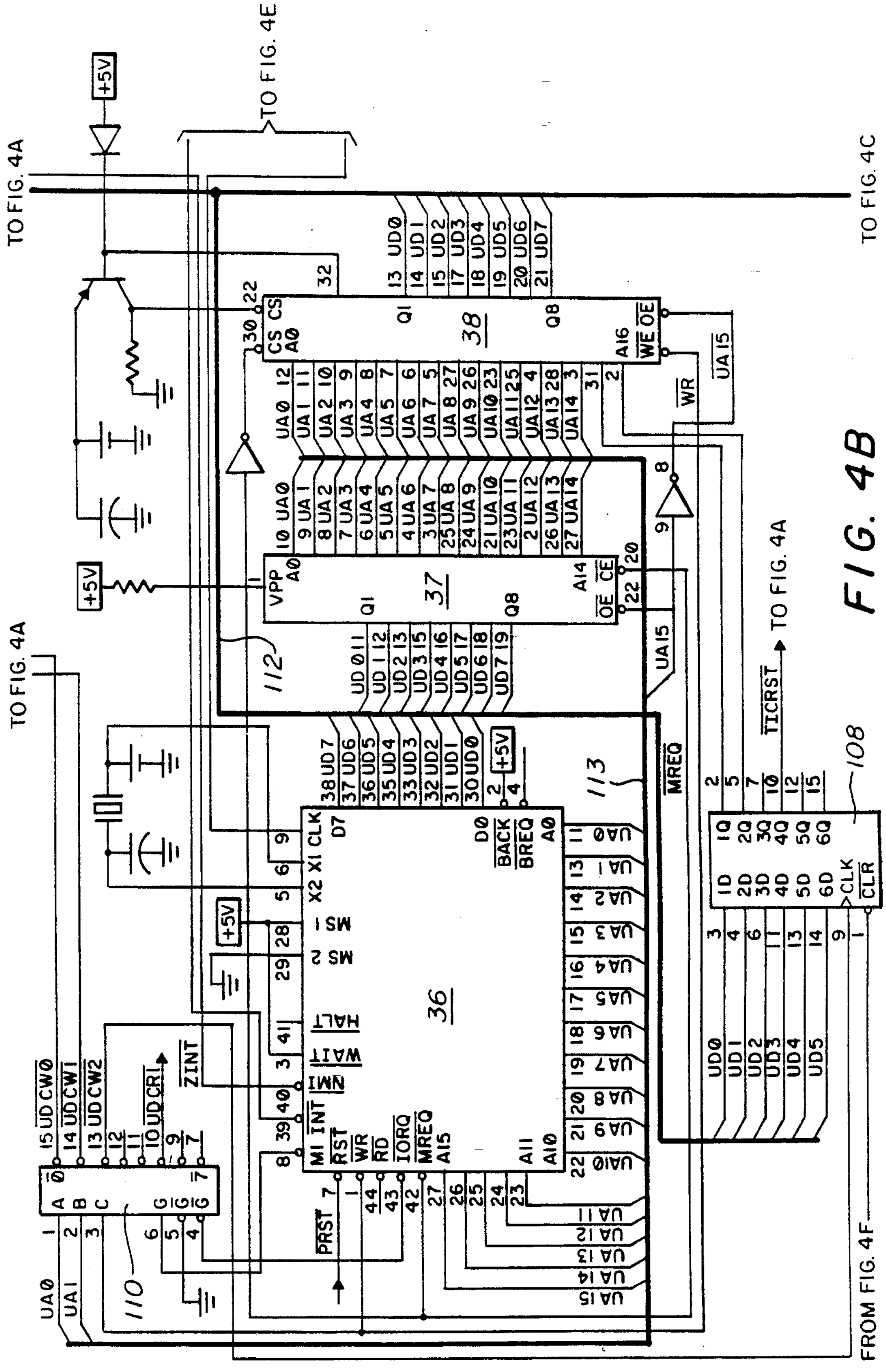
Figure 4C:
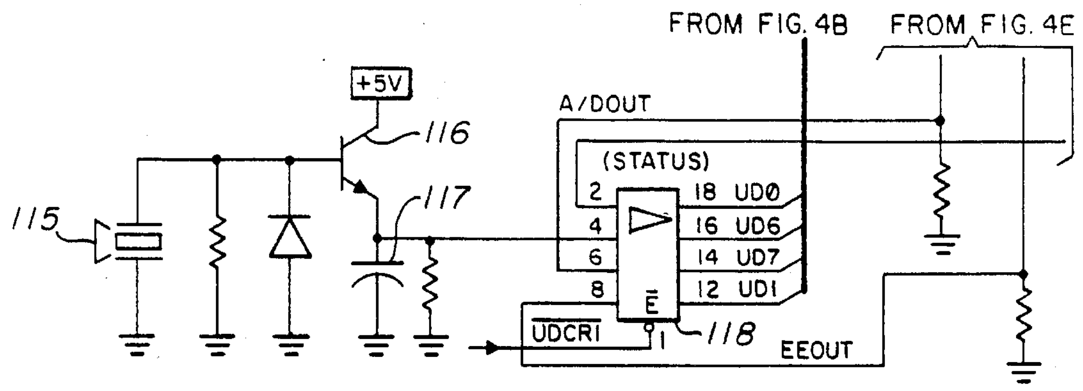
Figure 4D:
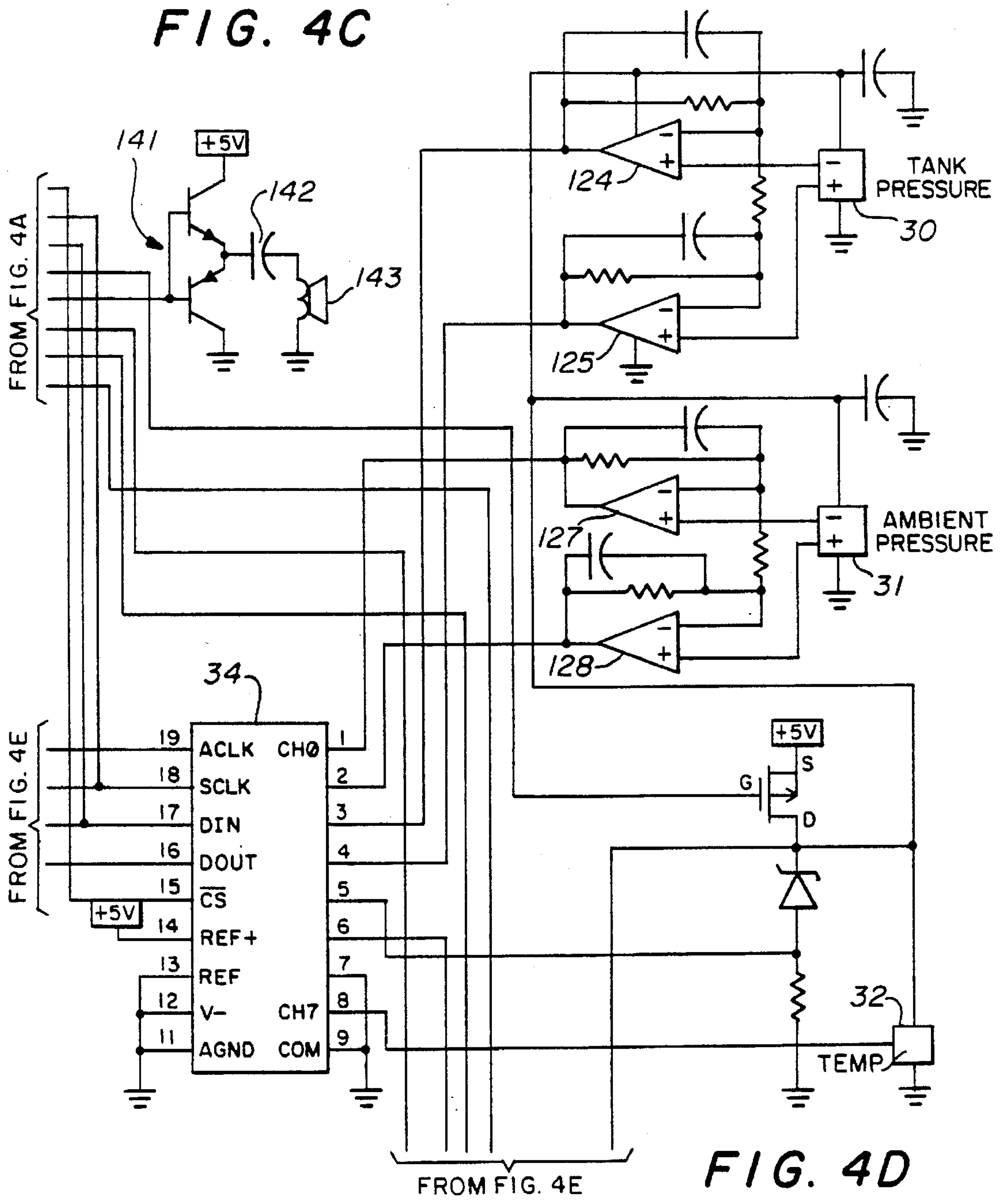
Figure 4E:
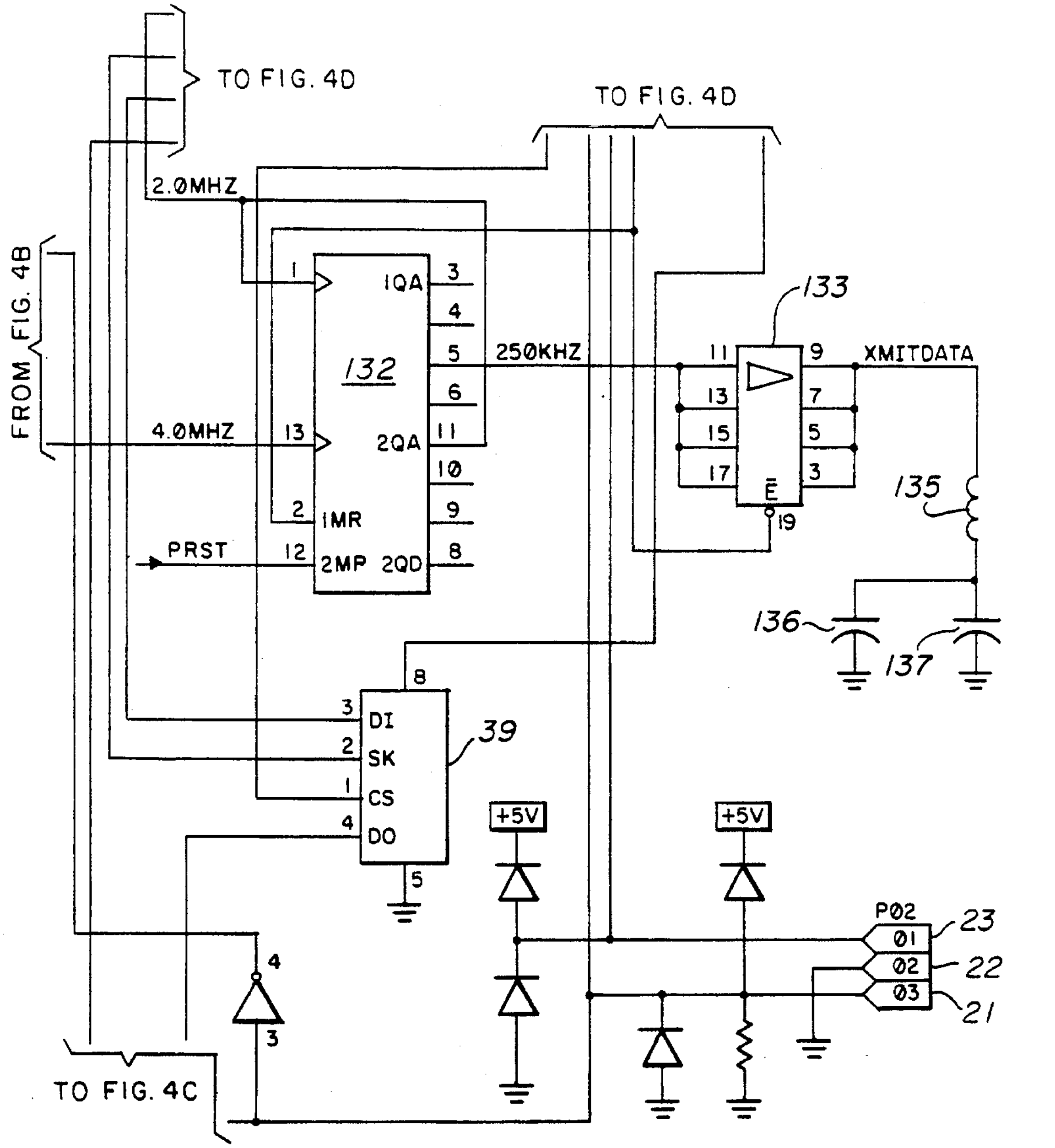
Figure 4F:
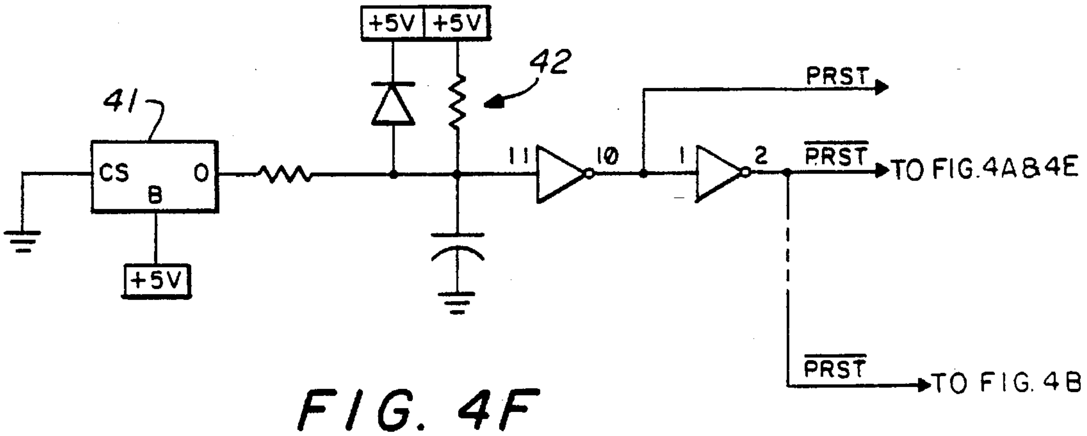

FIG. 3 is a block diagram that illustrates the functional elements of the dive computer display unit 25 shown in FIG. 1. Display unit 25 includes at least a receiver 50 for receiving the signal transmitted by transmitter 33 of tank unit 20 and a liquid crystal display (LCD) 55 for displaying dive parameter information to the user. In the preferred form, the display unit also includes a microcomputer 60 that is used to control operation of the display unit and drive the LCD 55. In the preferred form, microcomputer 60 consists of a microcontroller that is capable of driving LCD 55. Microcomputer 60 may, however, be implemented using a microprocessor with external memory and a separate device capable of driving LCD 55 or a microcontroller and a separate device capable of driving LCD 55. Moreover, many of the functions performed by microcomputer 35 located in tank unit 20 may be performed by microcomputer 60, in which case microcomputer 35 may be eliminated.

Detailed Description of the Tank Unit 20

FIGS. 4A through 4F form an electrical schematic of the dive computer tank unit 20 shown in FIG. 1. In the preferred form, timing circuit 43, includes a crystal 102 that produces a 32768 Hz signal. This signal is amplified and passed through buffer 103, which consists of transistor 104 and inverter 105, to the input of fourteen-stage divide-by-two counter 106. In the preferred form, counter 106 is a 74HC4020 high speed CMOS device available from integrated circuit manufactures such as TI and Motorola. The function of counter 106 is to divide the 32768 Hz signal by two, fourteen times to generate a 2 Hz signal for input to the clock input of D-type register 107, which functions as a one-stage divide-by-two counter. In the preferred form D-type register 107 is a 74HC74 with its Q-output unconnected and its Q_bar-output connected to its D-input. Also, the set pin of register 107 is connected to a +5 volt source and the reset pin is connected to six-bit latch 108 by control signal TICRST_bar. In the preferred form, six-bit latch 108 is a 74HC174. The function of control signal TICRST_bar is to suspend normal dive computer operations when the tank unit is attached to a personal computer through a data probe and the dive computer is communicating with the personal computer. (Communication between the dive computer and a personal computer through a data probe is discussed fully below.) During normal operation, the Q_bar-output of register 107 is a 1 Hz signal that is also connected to the clock-input of D-type register 109. In the preferred form, D-type register 109 is also a 74HC74. The D-input of register 109 is connected to ground so that during normal operation the Q-output of register 109 is a one pulse per second signal ZINT_bar. The set pin of register 109 is connected to a +5 volt source and the reset pin is coupled to microprocessor 36 through decoder 110, which is connected to the reset pin of register 109 by control signal UDCW0_bar. The function of control signal UDCW0_bar is to suspend control signal ZINT_bar when the dive computer performs a write operation to I/O address 0.

The ZINT_bar signal connects register 109 to a non-maskable interrupt pin of microprocessor 36. In the preferred form, microprocessor 36 is a Zilog Z84C01, which is a fully static device that draws an extremely low amount of current when not processing data. The function of the ZINT_bar signal is to cause microprocessor 36 to "wake-up" and perform its normal dive computer operations. If the tank unit has been turned on, when microprocessor 36 receives the ZINT_bar signal, it transmits the user's dive parameters for the previous "awake" period, calculates and stores the user's current dive parameters and then "goes back to sleep." (The advantage of transmitting the user's previous dive parameters and then calculating and storing the user's current dive parameters is discussed in detail below.) If the tank unit is off, when microprocessor 36 receives the ZINT_bar signal, it increments its internal clock, interrogates data bus 112 to determine whether it has been turned on and if it has not been turned on "goes back to sleep." In either case, during normal operation, microprocessor 36 "sleeps" until it again receives a ZINT_bar signal. In the preferred form, it takes a fraction of a second for microprocessor 36 to perform its normal dive computer operations and then go back to sleep. Thus, even when the tank unit is being used during a dive, it is only "awake" and consuming power a fraction of the time, which results in considerable power savings.

Microcomputer 35 Architecture

Microprocessor 36 is connected to data bus 112, which is an eight-bit bus with lines designated UD0 through UD7, and address bus 113, which is a sixteen-bit bus with lines designated UA0 through UA15. Data bus 112 connects microprocessor 36 to 32K byte read only memory (ROM) 37 and a 128K byte random access memory (RAM) 38. In the preferred form, ROM 37 is a 27C256, which is a 32,768×8 bit electrically programmable read only memory (EPROM) available from Intel, and RAM 38 is a SRM20100, which is a 131,072×8 bit static random access memory available from S-MOS. A computer program of conventional form stored in ROM 37 controls operation of microprocessor 36. Lines UA0 through UA14 of address bus 113 connect microprocessor 36 to ROM 37 and RAM 38. Moreover, line UA15 of address bus 113 connects microprocessor 36 to output enable pin (OE_bar) of ROM 37 and, after passing through an inverter, is connected the output enable pin (OE_bar) of RAM 38 as UA15_bar. Lines UD0 through UD5 are also connect microprocessor 36 to six-bit latch 108 to allow microprocessor 36 to map the 128K bytes of available memory into four 32K byte segments. Through six-bit latch 108, microprocessor 36 generates address lines A15 and A16, which determine which of the four 32K byte segments of the 128K byte RAM 38 is accessed. The memory request pin (MREQ_bar) of microprocessor 36 is connected to ROM 37 through its chip enable pin (CE_bar) and, after passing through an inverter, is connected to RAM 38 through its chip select pin (CS_bar) as MREQ. Also, the write pin (WR_bar) of microprocessor 36 is connected to RAM 38 through its write enable pin (WE_bar). As noted above, a computer program of conventional form is stored in ROM 37. RAM 38 is used to store data.

As noted above, six-bit latch 108 generates address lines A15 and A16, which determine which of the four 32K byte segments of the 128K byte RAM 38 is accessed. Six-bit latch 108 also generates control signal TICRST_bar, which is used to suspend normal operation of the dive computer when it is communicating to a personal computer through a data probe. Six-bit latch 108 is connected to microprocessor 36 by lines UD0 through UD5 of data bus 112 and through decoder 110 by control signal UDCW2_bar, which is connected to the clock pin of six-bit latch 108. The function of control signal UDCW2_bar is to cause the data values present on lines UD0 through UD5 of data bus 112 to be latched onto the outputs of six-bit latch 108.

Data bus 112 also connects microprocessor 36 to eight-bit latch 114, through which microprocessor 36 controls certain operations of the tank unit that will be discussed in detail below. In the preferred form, eight-bit latch 114 is a 74HC273. The clock input of eight-bit latch 114 is coupled to microprocessor 36 through decoder 110, which is connected to eight-bit latch 114 by control signal UDCW1_bar. The function of control signal UDCW1_bar is to cause the data values present on data bus 112 to be latched onto the outputs of eight-bit latch 114.

Decoder 110 is connected to microprocessor 36 by lines UA0 and UA1 of address bus 113 and by lines that connect to pins IORQ_bar, WR_bar and M1 of microprocessor 36. Through these connections, microprocessor 36 generates three separate write control signals (UDCW0_bar, UDCW1_bar and UDCW2_bar) and one read control signal (UDCR1_bar), which are the only write and read operations performed by microprocessor 36. In the preferred form, decoder 110 is a 74HC138.

Microprocessor 36 operates at a frequency of 4 MHz. In the preferred form, the clock generator circuit for microprocessor 36 includes a 4 MHz crystal, which is connected to pins X1 and X2 of microprocessor 36.

The Tank Unit "Tap On" Circuit 40

In the preferred form, the tank unit includes a "tap on" switch 40 that allows the user to turn the tank unit on by tapping the area marked on the outside of the case. (The tank unit automatically turns itself off when the nitrogen levels of the twelve tissue compartments approach normal, or after one hour, whichever is longer.) One of the advantages of using a "tap-on" switch 40 is that it eliminates the sealed penetration of the case required for a conventional on-off switch and, thus, minimizes the risk of flooding.

The "tap-on" switch 40 is activated by the user tapping on the area marked on the outside of the tank unit case. Piezoelectric element 115 is mounted to the inside of the tank unit case opposite the marked area for the switch. In the preferred form, piezoelectric element 115 is a device manufactured by Murata Products (part no. 71313-27-4). When the user taps the marked area, piezoelectric element 115 senses the vibration and generates a signal that causes transistor 116 to turn on, which in turn charges capacitor 117. Capacitor 117 is connected to an input of gated-buffer 118, which controls the status of the tank unit 20. In the preferred form gated-buffer 118 is one-half of a 74HC244, which has four inputs and four outputs. The outputs of gated-buffer 118 are connected to four of the eight data lines that make up data bus 112. These four data lines, UD0, UD1, UD6 and UD7, are the only data lines that can be read by microprocessor 36 and are used to control which operation is performed by the tank unit. The enable pin (E_bar), of gated-buffer 118 is connected to decoder 110 by control line UDCR1_bar. The function of UDCR1_bar is to cause gated-buffer 118 to transfer the data values present at the inputs to the outputs so that they can be read by microprocessor 36. When capacitor 117 is charged, activation of control line UDCR1_bar causes gated-buffer 118 to set a positive signal on data bus 112 line UD6.

As noted above, if the tank is off, when it receives control signal ZINT_bar, microprocessor 36 increments its internal clock and then interrogates data bus 112 to determine whether it has been turned on. If the user has tapped the area marked on the outside of the case during the previous second, the charge on capacitor 117, is transferred by gated-buffer 118 to data line UD6, which is read by microprocessor 36 to an internal register. Once the data has been read into an internal register, microprocessor 36 performs a test-bit operation to determine whether the tank unit has been turned on. When microprocessor 36 determines that the tank unit has been turned on, it begins its normal dive computer operations. (If the tank unit has been turned on and senses that ambient pressure corresponds to sea level or zero depth, the unit defaults to surface mode.) After the tank unit is turned on, it begins transmitting the user's dive parameters to the display unit and calculating and storing the user's current dive parameters each time it receives a ZINT_bar signal from register 109.

Dive Parameters

In the preferred form, the tank unit includes at least means for measuring the air-pressure in the user's compressed-air tank 13, ambient pressure and ambient temperature.

The pressure in the user's compressed-air tank 13 is measured by transducer 30, which in the preferred form is located outside the case of the tank unit in the connector that connects the tank unit to high pressure port 19 of first stage regulator 15. In the preferred form, transducer 30 is a high-pressure transducer available from Luca Nova Sensors (part no. NPI-15X-C00XXX), which is capable of providing a linear measurement of pressure from zero to 4000 psi. (The threads of transducer 30 are modified to match a standard first stage regulator connection.) Four wires connect transducer 30 to the interior of the tank unit. One wire 120 connects transducer 30 to a +5 volt source through p-channel power MOSFET 121. Two more wires, 122 and 123, connect the differential outputs of transducer 30 to the positive inputs of operational amplifiers (op-amps) 124 and 125, respectively. In the preferred form op-amps 124 and 125 are both LPC660s available from National Semiconductor. The fourth wire 126 connects transducer 30 to ground. Op-amps 124 and 125 are connected in the conventional fashion to amplify the differential outputs of transducer 30. The outputs of op-amps 124 and 125 are connected to A/D converter 34.

Ambient pressure is measured by transducer 31, which is mounted on the inside of the tank unit case and is electrically connected in the same manner as transducer 30. In the preferred form, transducer 31 is a low-pressure transducer available from Sen-Sym (part no. SX100A), which is capable of providing a linear measurement of pressure from zero to 100 psi. Four wires connect to transducer 31. Wire 120, which connects transducer 30 to a +5 volt source through p-channel power MOSFET 121, also connects transducer 31 to that +5 volt source through MOSFET 121. Two more wires, 127 and 128, connect the differential outputs of transducer 31 to the positive inputs of op-amps 129 and 130, respectively. In the preferred form op-amps 129 and 130 are both LPC660s. The fourth wire connects transducer 31 to ground. Op-amps 129 and 130 are connected in the conventional fashion to amplify the differential outputs of transducer 31. The outputs of op-amps 129 and 130 are connected to A/D converter 34.

Ambient temperature is measured by temperature sensor 32, which is physically attached to one of the low pressure hose clasps. In the preferred form, temperature sensor 32 is a LM34DZ available from National Semiconductor. Three wires connect to temperature sensor 32. Wire 120, which connects transducers 30 and 31 to a +5 volt source through p-channel power MOSFET 121, also connects to temperature sensor 32. A second wire attaches temperature sensor 32 to ground. And the third wire 131 connects the output of the temperature sensor 32 to A/D converter 34.

P-channel power MOSFET 121 is coupled to microprocessor 36 through eight-bit latch 114, which is connected to microprocessor 36 by data bus 112. Specifically, the input to eight-bit latch 114 on line UD4 controls whether MOSFET 121 is turned on. MOSFET 121 is only turned on to measure the user's dive environment, which minimizes the power used by the tank unit and maximizes the battery life of the tank unit.

In the preferred form, A/D converter 34 is a LTC1290, which is a serial device available from Linear Technologies Corporation. A/D converter 34 receives analog dive parameter measurements from high-pressure transducer 30, ambient-pressure transducer 31 and temperature sensor 32, converts those measurements to digital data and transmits that data to microprocessor 36 through gated-buffer 118. The serial output pin (DOUT) of A/D converter 34 is connected to the input of gated-buffer 118, which transfers that data onto line UD7 when control line UDCR1_bar is activated by microprocessor 36. Serial data is shifted out of A/D converter 34 and through gated-buffer 118 in accordance with the shift clock (SCLK) signal, which is generated by microprocessor 36 through eight-bit latch 114.

A/D converter 34 is a successive approximation type device, which requires a clock input (ACLK). The clock input of A/D converter 34 is provided by microprocessor 36 through divider 132. One of the functions of divider 132 is to receive a 4 MHz signal from microprocessor 36 and divide it by two to generate a 2 MHz signal for A/D converter 34. (Divider 132 also takes this same 2 MHz signal and divides it by eight to generate a 250 KHz signal that is used by the tank unit to transmit to the display unit 25.)

A/D converter 34 is also coupled to microprocessor 36 through eight-bit latch 114 by the data-in pin (DIN) and the chip-select pin (CS_bar). The DIN connection allows microprocessor 36 to write data to A/D converter 34 and the chip-select connection allows microprocessor 36 to choose between A/D converter 34 and electrically alterable read only memory (EAROM) 39, which shares the data in and shift clock connections of A/D converter 34.

Breathing Parameter Calculations

In addition to monitoring the user's conventional dive parameters, such as the depth of the user, the air pressure in compressed-air tank 13, and the length of time that the user can safely remain at that depth, microcomputer 35 also computes the user's breathing parameter, which is the rate at which the air pressure in compressed-air tank 13 is decreasing normalized for depth. For example, if the user is on the surface and is breathing such that air pressure in compressed-air tank 13 is decreasing at a rate of 20 psi per minute, then the user's breathing parameter will be 20. If the user is at a depth of 66 feet and is breathing at the same rate, such that the air pressure in compressed-air tank 13 is decreasing at a rate of 60 psi per minute, the user's breathing parameter will still be 20. By eliminating the variable of depth, the user can monitor his actual rate of air consumption.

Figure 6:
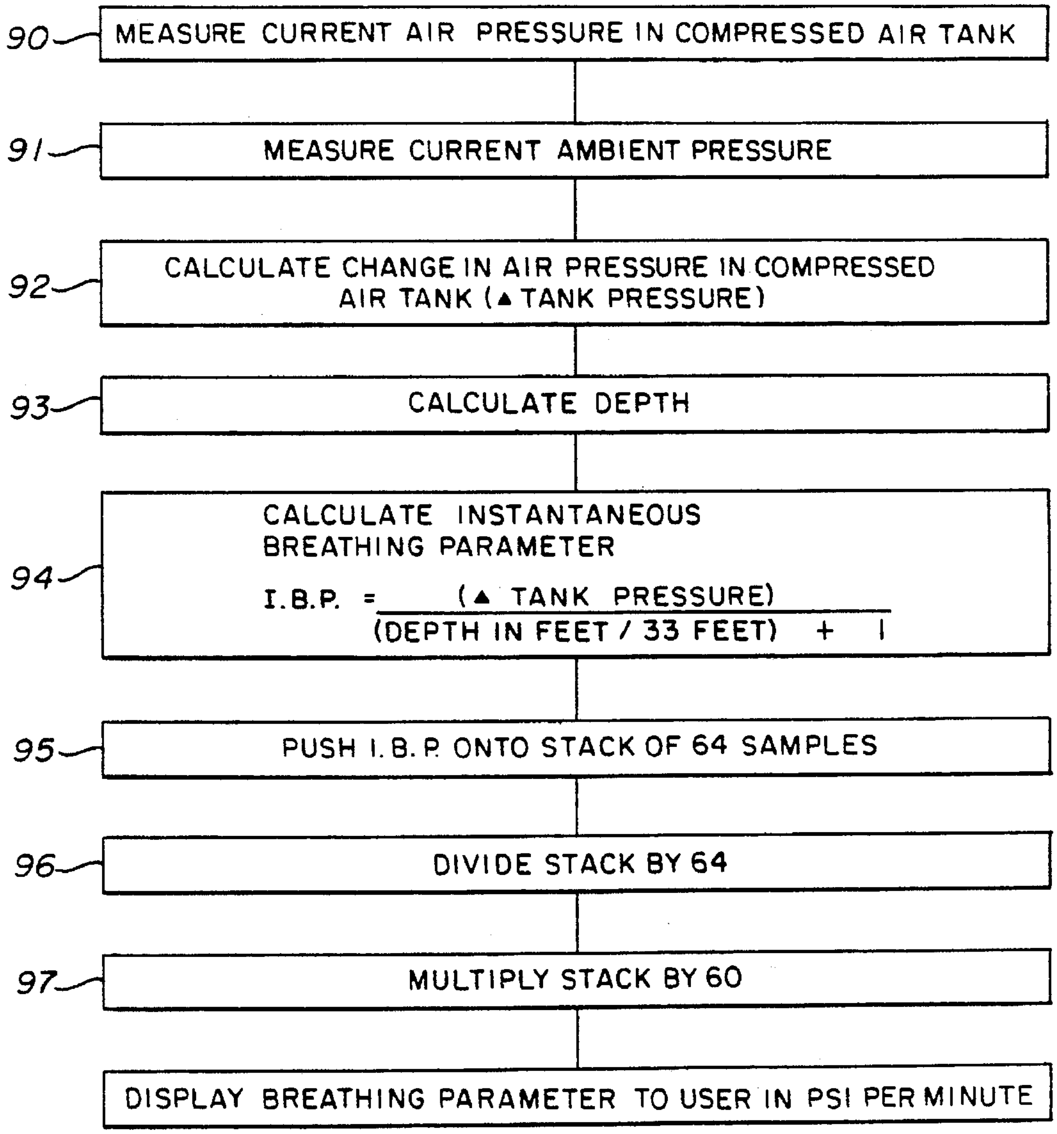
FIG. 6 is a flow chart that illustrates the preferred method of calculating the user's breathing parameter.

FIG. 6 is a flow chart that illustrates the preferred method of calculating the user's breathing parameter. In the preferred form, high pressure transducer 30 periodically measures the air pressure in compressed-air tank 13 and generates an analog signal that is converted by A/D converter 34 into a digital signal for use by microcomputer 35. (Block 90.) During the same time period, low pressure transducer 31 measures ambient pressure and generates an analog signal, which is also coupled to microcomputer 35 through A/D converter 34. (Block 91.) Microcomputer 35, calculates the change in air pressure in compressed air tank 13 (Δ tank pressure) by subtracting the air pressure reading of the previous time period from the air pressure reading of the current time period. (Block 92.) Microcomputer 35 also calculates the user's current depth based on the ambient pressure reading measured by transducer 31. (Block 93.) With this information, microcomputer 35 calculates the user's instantaneous breathing parameter, which is equal to the change in tank pressure normalized for depth (Block 94):

$$I.B.P. = \frac{(\Delta \text{ tank pressure})}{(\text{depth in feet}/33 \text{ feet}) + 1}$$

Microcomputer 35 calculates the user's breathing parameter by averaging the user's current instantaneous breathing parameter with the user's previous sixty-three (63) instantaneous breathing parameters, which are stored in memory. (Blocks 95 and 96.) Averaging the user's instantaneous breathing parameter over a 64 second period eliminates rapid variations that may occur in the user's instantaneous breathing parameter. The user's average breathing parameter is then multiplied by 60 so that the actual breathing parameter displayed to the user is indicative of the rate at which the pressure in compressed-air tank 13 is decreasing in psi per minute normalized for depth. (Block 97.)

Alternatively, the user's breathing parameter can be calculated by summing the user's current instantaneous breathing parameter with the user's previous fifty-nine (59) instantaneous breathing parameters, which are stored in memory. This method eliminates the need to divide by 64 and multiply by 60, and still results in a breathing parameters being displayed to the user, which is indicative of the normalized rate at which the pressure in compressed-air tank 13 is decreasing in psi per minute.

Operational Parameters

The operational parameters of the dive computer 12 are stored in the tank unit in EAROM 39. In the preferred form, EAROM 39 is a NMC93C66, which is a 4096 bit EAROM available from National Semiconductor. EAROM 39 is coupled to microprocessor 36 through eight-bit latch 114. As noted above, EAROM 39 shares its data in (DIN) and shift clock (SCLK) connections to microprocessor 36 with A/D converter 34. EAROM 39 is also coupled to microprocessor 36 through eight-bit latch 114 by a chip select pin (CS_bar), which allows microprocessor 36 to choose between EAROM 39 and A/D converter 34. EAROM 39 is also coupled to microprocessor 36 through gated-buffer 118. The Data Out pin (DO) of EAROM 39 is connected to the input of gated-buffer 118, which transfers data transmitted from EAROM 39 onto data bus 112 when control line UDCR1_bar is activated by microprocessor 36. Serial data is shifted out of EAROM 39 and through gated-buffer 118 in accordance with the shift clock (SCLK) signal, which, as noted above, is generated by microprocessor 36 through eight-bit latch 114.

In the preferred form, the user can customize the operational parameters of dive computer 12 by setting various control bits that control execution of the dive computer control program stored in ROM 37. (The user access's EAROM 39 by connecting the tank unit 20 to a personal computer 200 through data probe 150. Data probe 150 and the connection of the dive computer tank unit 20 to a personal computer 200 through data probe 150 are discussed in detail below.) By setting various control bits in EAROM 39, the user can select whether information is displayed in english or metric units and if the user chooses to display information in metric units, the user can further select whether pressure is displayed in bars or kg/cm$^2$. In the preferred form, the user can also select the rate at which dive parameter information is stored by the dive computer tank unit 20 and the length of time the display unit 25 displays information in alternate modes of operation. Moreover, the user can control the method used by the dive computer to model nitrogen compartments and select whether the dive computer modifies the method it uses to model nitrogen compartments depending other variables, such as the ambient temperature of the water or changes in the user's breathing parameter. The user can also control whether the dive computer sounds an audible alarm and the circumstances under which the dive computer sounds an audible alarm.

In the preferred form, each dive computer has an identification number stored in EAROM in both the tank unit 20 and the display unit 25. This identification number is used to ensure the integrity of the communication link between the tank unit and the display unit. The dive computer identification number stored in EAROM 39 is included in each transmission from the tank unit 20 to the display unit 25. The same dive computer identification number is also stored in EAROM in the display unit 25. When the display unit 25 receives a transmission from the tank unit 20, it first compares the identification number transmitted with the signal to determine if it originated at its tank unit 20. If the identification number transmitted by the tank unit 20 matches the identification number of the display unit 25, the display unit 25 displays the information contained in that transmission. If, however, the identification numbers do not match, the display unit 25 discards the transmitted information. Thus, if the display unit 25 receives a signal from a nearby tank unit that is not the user's, it will not mislead the user by displaying the information contained in that signal. In the preferred form, the user can change the identification number transmitted by the tank unit by accessing EAROM 39 through data probe 150, so that a single tank unit can be used with other display units or display devices.

Power for EAROM 39 is supplied through P-channel power MOSFET 121, which minimizes the power used by EAROM 39 and helps to maximize the battery life of the tank unit.

The Tank Unit Data Probe Connection

As noted above, the tank unit includes three metal clasps 21 through 23 that may be used during a dive to connect the tank unit 20 to the user's low pressure hose 24. These three metal clasps 21 through 23 can also be used to connect the dive computer to a personal computer 200 through the data probe 150. As noted above, the user can then select the operational parameters of the dive computer 12. This connection can also be used to download stored information from the tank unit 20 to a personal computer 200.

Metal clasp 21 is used to transmit serial data from personal computer 200 to the tank unit 20. It is connected to data bus 112 through gated-buffer 118. As noted above, microprocessor 36 transmits control signal UDCR1_bar to transfer the data at the inputs of gated-buffer 118 onto data bus 112, where it can be read. Thus, microprocessor 36 can serially read data from metal clasp 21 through gated-buffer 118. Metal clasp 23, which is connected to microprocessor 36 through eight-bit latch 114, is used to transmit serial data from the tank unit to the personal computer. Metal clasp 22 is electrically connected to ground.

The data probe 150 used to connect the tank unit 20 to personal computer 200 is illustrated in FIGS. 10 and 11.

Tank Unit Transmitter Circuit 33

As noted above, divider 132 receives a 4 MHz signal from microprocessor 36, which it first divides by two and then divides by eight to generate a 250 KHz signal that is used to transmit data to the display unit. The 250 KHz signal generated by divider 132 is connected to buffer/driver 133. In the preferred form, buffer/driver 133 is one-half of a 74HC244. Microprocessor 36 is also coupled to the enable pin (E_bar) of buffer/driver 133 through eight-bit latch 114. This connection between microprocessor 36 and buffer/driver 133 is used by microprocessor 36 to modulate the 250 KHz signal with dive parameter data to be transmitted to the display unit. In the preferred form, a pulse code modulation technique is used to modulate the 250 KHz signal received by buffer/driver 133. The signal generated by buffer/drive 133 is connected to the tank unit antenna 134. In the preferred form, tank unit antenna 134 consists of inductor 135, which is made up of a ferrite core wrapped by approximately 60 turns of a #30 gage copper wire, connected in series with two capacitors, 136 and 137, which are also connected in parallel to ground. Capacitors 136 and 137 are tuned to impedance match the antenna at the desired transmission frequency. Antenna 134 generates a modulated magnetic field that inductively couples inductor 135 in the tank unit transmitter circuit to an inductor located in receiver circuit 50 contained in the display unit 25.

Tank Unit Alarm Circuit 140

The tank unit alarm circuit 140, includes buffer 141, which consists of two transistors, capacitor 142 and speaker 143. In the preferred form, speaker 143 is a standard 8 ohm speaker available from Shogyo International (part no. CP-28CT). Tank unit alarm circuit 140 is coupled to microprocessor 36 through eight-bit latch 114. The tone generated by speaker 143 corresponds to the frequency at which microprocessor 36 alternates the bit coupled to buffer 141. In the preferred form, microprocessor 36 sweeps the rate at which it alternates the bit coupled to buffer 141 from a low audible frequency to a high audible frequency over a one-half second period, once every second for five seconds. Thus, the warning signal generated by the tank unit is a one-half second sweep by speaker 143 from a low tone to a high tone, once every second for five second.

In the preferred form the tank unit alarm circuit sounds an audible alarm whenever certain dive parameters, such as the amount of air left in the user's compressed-air tank, reach dangerous levels. Specifically, the tank unit alarm circuit sounds an audible alarm if the diver's breathing parameter suddenly undergoes a rapid change or reaches an extremely high or low level. In the preferred form, the user can select which dive parameters cause an audible alarm to sound and set the dive parameter levels at which the audible alarm sounds by setting various control bits in EAROM 39.

Low Battery Detect 41 and Power Up Reset Circuit 42

The tank unit includes a low battery detect 41 and power up reset circuit 42 to ensure proper operation of the dive computer. In the preferred form, low battery detect circuit 41 consists of a SCI17701J available from S-MOS, which transmits a signal that holds microprocessor 36 at reset whenever the batteries in the tank unit are low. The power up reset circuit 42 includes a diode and resistor connected in parallel to a +5 volt source and through a capacitor to ground. When the user changes the batteries in the tank unit, this circuit causes a reset signal to be sent to microprocessor 36. Whenever microprocessor 36 receives a reset signal it automatically runs a self test diagnostic program to ensure that the tank unit is functioning properly.

Automatic Depth Calibration

The same three metal clasps 21 through 23 that are used to connect the tank unit to the user's low pressure hose 24 during a dive and to data probe 150, are also used to calibrate the dive computer's depth measurements for fresh water and sea water. When the tank unit detects that it has been submerged, microprocessor 36 transmits a +5 volt pulse into the surrounding water through metal clasp 23 and measures the voltage signal detected at metal clasp 21. In addition to being coupled to microprocessor 36 through gate-buffer 118, metal clasp 21 is also coupled to microprocessor 36 through A/D converter 34. Since sea water is a better conductor than fresh water, the tank unit can determine the salinity of the water into which it has been submerged by the strength of the signal received at metal clasp 21. After microprocessor 36 determines whether the user is in sea water or fresh water, it stores that information and calibrates its depth measurements accordingly. In the preferred form, the calibration process takes place only after tank unit 20 has been submerged a depth of approximately five feet. This process is repeated, however, each time the tank unit 20 is submerged.

Detailed Description of the Display Unit 25

Figure 5A:
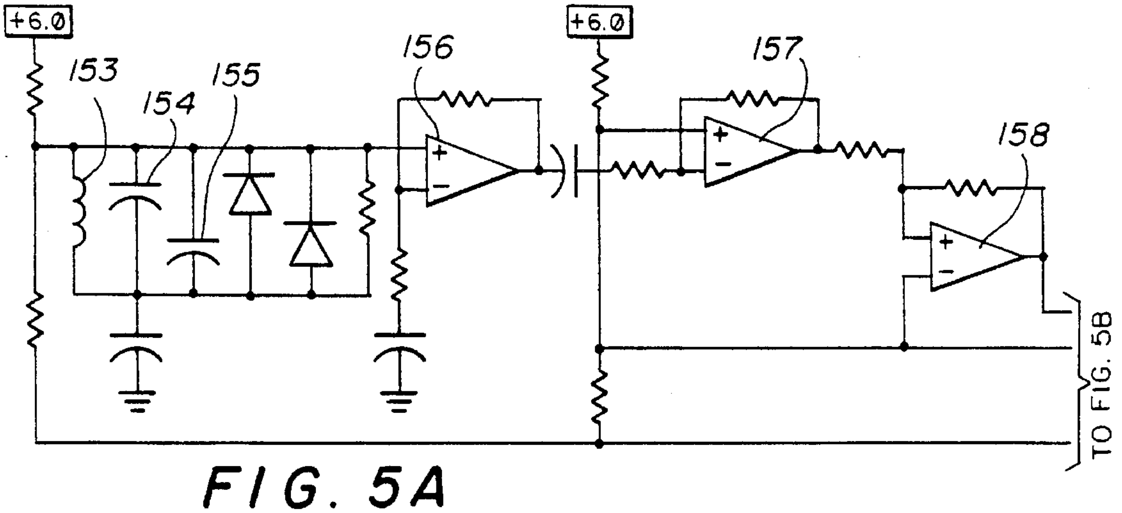
Figure 5B:
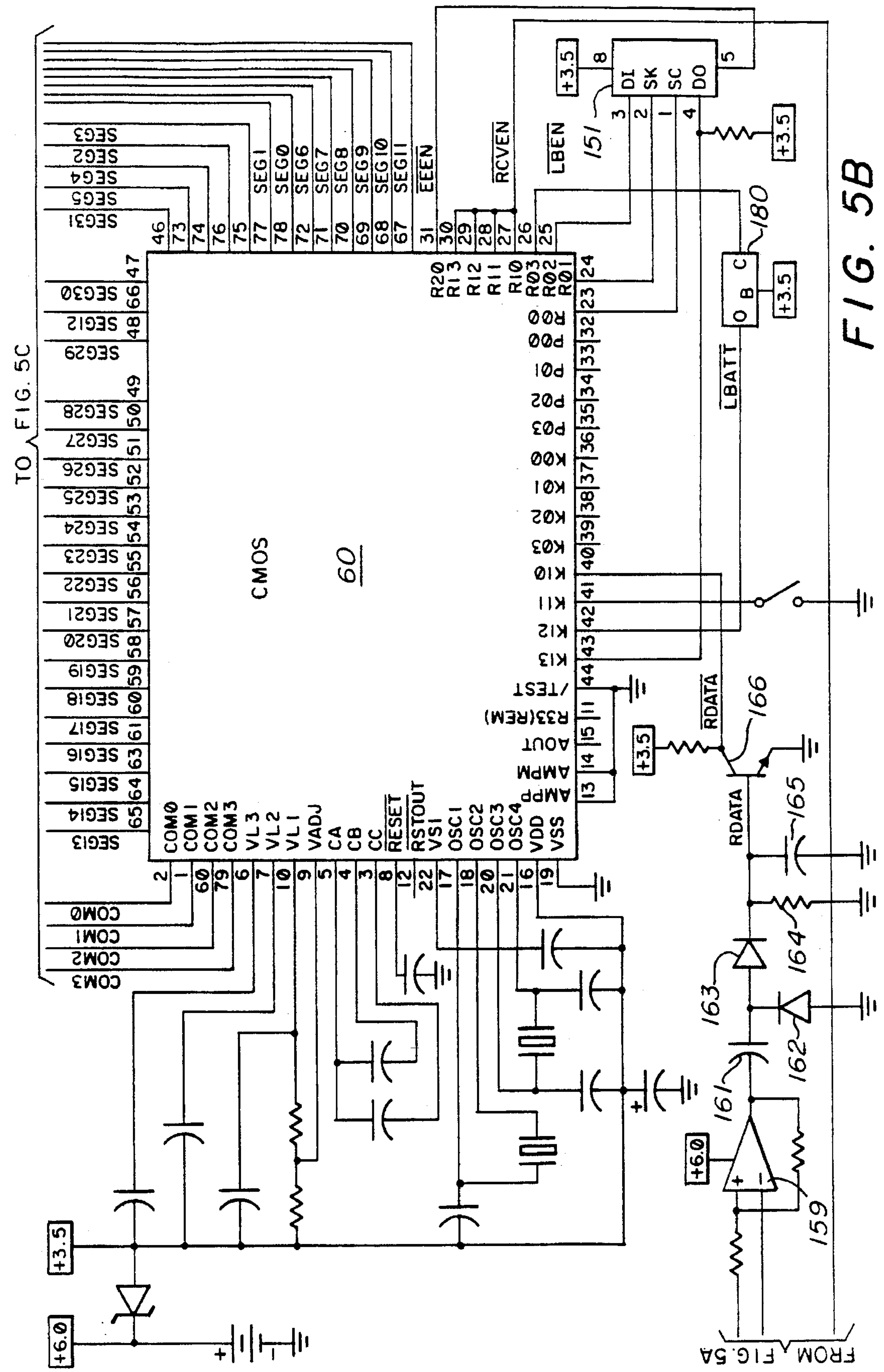

FIGS. 5A through 5C form an electrical schematic of the display unit 25 of the dive computer shown in FIG. 1. Operation of the display unit is controlled by microcomputer 60, which is a four bit microcontroller capable of driving a liquid crystal display 55. In the preferred form, microcomputer 60 is a S-MOS SMC6214. As noted above, microcomputer 60 is a single chip device that includes a 4096×12 bit ROM and a 208×4 RAM. The ROM of microcomputer 60 contains a computer program of conventional form that controls operation of microcomputer 60. Also, as noted above, the display unit includes EAROM 151, which contains the identification number of the display unit 25. EAROM 151 is directly connected to microcomputer 60. In the preferred form, the EAROM 151 is a NMC93C06, which is a 256 bit EAROM available from National Semiconductor.

The Display Unit Receiver Circuit 50

The display unit includes an antenna 152 that receives the modulated magnetic field generated by the tank unit antenna 37. In the preferred form, the display unit antenna 152 consists of inductor 153, which is formed by a ferrite core wrapped by approximately 100 turns of a #30 gage copper wire, connected in parallel with two capacitors, 154 and 155, which are also connected in parallel. Capacitors 154 and 155 are tuned to impedance match the display unit antenna 152 at the desired transmission frequency. As noted above, in the preferred information is transmitted from the tank unit to the display unit by a 250 KHz modulated magnetic field. Specifically, the magnetic field generated by the tank unit antenna induces a magnetic flux through the ferrite core of inductor 153, which in turn causes a current to be generated in the winding of inductor 153. The signal received by display unit antenna 152 is limited by back-to-back diodes to attenuate strong magnetic coupling between the tank unit 20 and the display unit 25 and coupled through a series of four op-amps 156 through 159, which translate the signal receive by the display unit into a modulated 250 KHz square wave. In the preferred form, each of the four op-amps is a TL064 available from either TI or Motorola.

The dive parameter data contained in the modulated signal received by the tank unit is extracted by demodulator 160. In the preferred form, demodulator 160 is a simple circuit that consists of capacitor 161 connected in series to diode 162, which is connected to ground, and through diode 163 to a resistor 164 and capacitor 165, which are connected in parallel to ground, and the gate of transistor 166. The source of transistor 166 is connected through a resistor to a +3.5 volt source and to an input to microcomputer 60 through data line RDATA_bar. The emitter of transistor 166 is connected to ground. The presence of a pulse on the output of op-amp 159 causes capacitor 165 to charge up and transistor 166 to turn on, which in turn causes data line RDATA_bar to be pulled to ground. The absence of a pulse on the output of op-amp 159 causes capacitor 165 to discharge to ground through resistor 164, which turns off transistor 166 and causes data line RDATA-bar to float high. In this fashion, the display unit microcomputer 60 receives the digital information transmitted by the tank unit microcomputer 36.

Figure 7A:
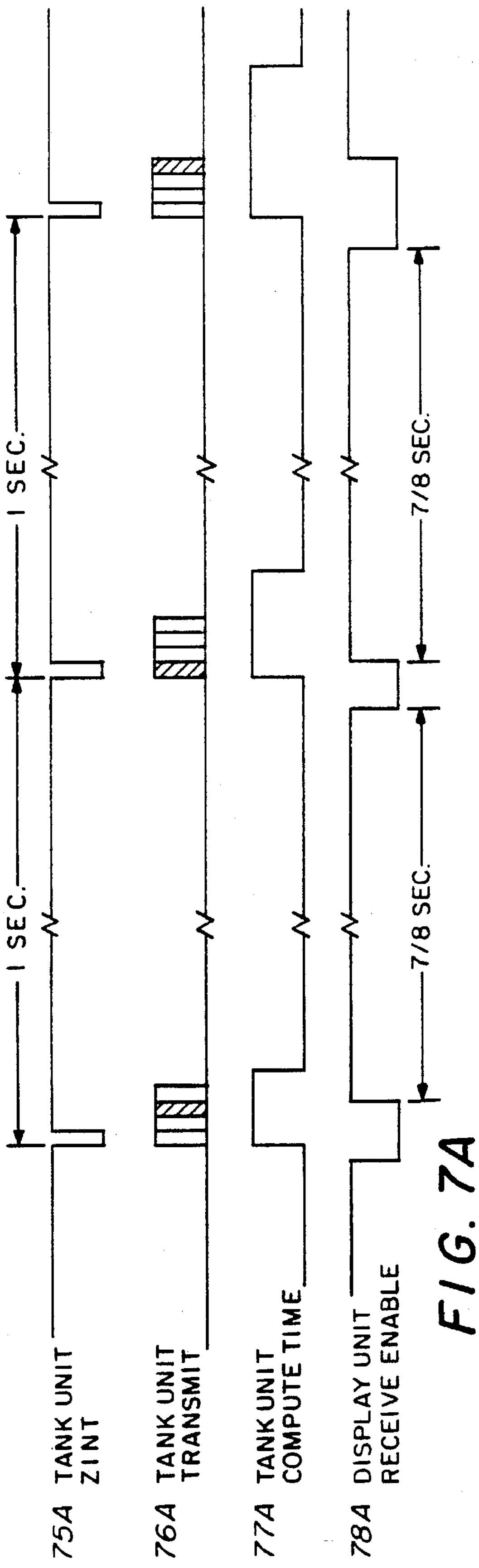
FIGS. 7A and 7B are timing diagrams that illustrate the relationship between the transmission of data by the tank unit and reception of data by the display unit of the dive computer.
Figure 7B:
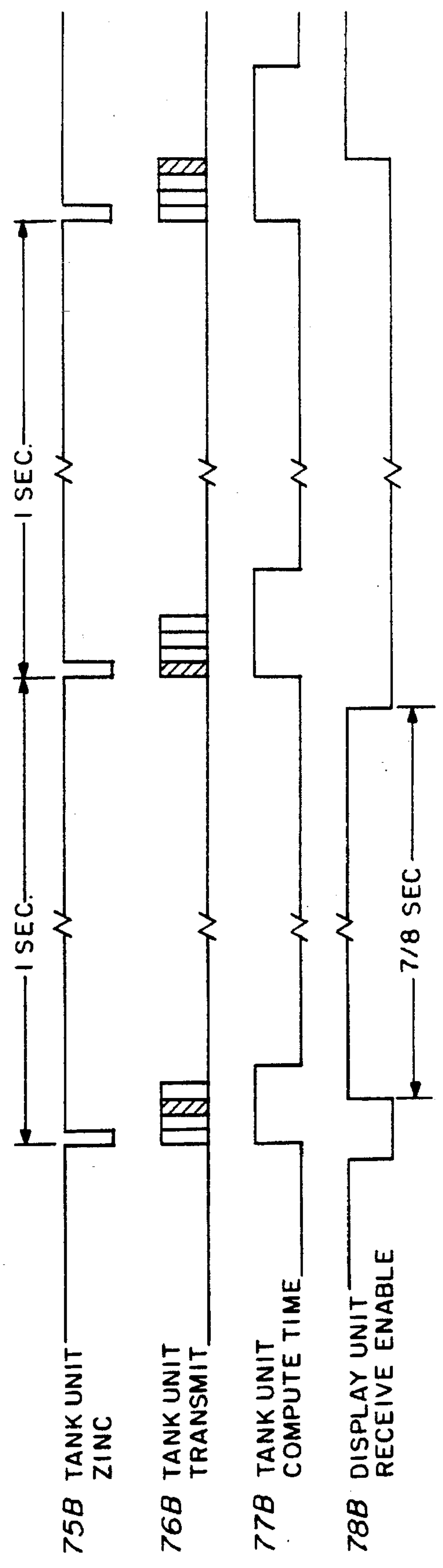

FIGS. 7A and 7B are timing diagrams that illustrate the relationship between data transmitted by the tank unit and data received by the display unit. FIG. 7A shows transmissions between the tank unit and display unit without error. Time line 75A illustrates the tank unit ZINT_bar signal, which occurs once every second. Time line 76A illustrates the tank unit transmit period. As noted above, when microprocessor 36 receives the ZINT_bar signal, it transmits the user's dive parameters from the previous "awake" period and calculates and stores the user's current dive parameters. Once every second, the ZINT_bar signal causes the tank unit 20 to transmit data in one of four possible time slots. The tank unit randomly chooses the time slot in which to transmit data. The cross-hatched area on time line 76A illustrates the tank unit sending data during the third, first and fourth time intervals of the tank unit transmit period. Time line 77A illustrates the tank unit compute period. After microprocessor 36 is "awakened" by the ZINT_bar signal, it immediately begins computing the user's current dive parameters. When it has transmitted the data from the previous "awake" period and computed and stored the user's current dive parameters, microprocessor 36 "goes back to sleep." As shown by time line 77A, although the tank unit transmit period is a set non-varying interval, the tank unit compute time varies according to the complexity of the computation required. Time line 78A illustrates the function of the display unit receive enable (RCVEN_bar) signal, which enables the display unit receiver circuit 50 seven-eighths (⅞) of a second after reception of the previous data transmission and disables the display unit receiver circuit 50 immediately after it receives the current data transmission. As shown by time line 78A, the time interval during which the receiver circuit 50 is enabled varies due to the random nature of the tank unit transmit period. Limiting the time period during which the display unit will accept data transmissions from the tank unit reduces the likelihood of the display unit receiving data from another user's tank unit.

FIG. 7B illustrates the ability of the display unit to recover from a missed reception. Time lines 75B through 77B are the same as time lines 75A through 77A. As shown by time line 78B, however, if the display unit does not receive a data transmission, in this case the second data packet, the receive enable signal continues to hold the display unit receiver circuit 50 open until the display unit receives the next data transmission, in this case the third data packet. After the display unit receives a data transmission, it immediately disables the display unit receiver circuit 50 and then enables the display unit receiver circuit 50 seven-eighths (⅞) of a second later. The display unit then continues to operate as illustrated by FIG. 7A. (In the preferred form, if the display unit fails to receive a data transmission for five seconds, it flashes the last data received from the tank unit.)

The Display 55

Returning to FIG. 5, microcomputer 60 is directly connected to a liquid crystal display 55 by four common lines and thirty-two segment driver lines. In the preferred form, liquid crystal display 55 is a twisted nematic type display with dark segments on a clear background and has a reflective type polarizer on the back of the display. Microcomputer 60 generates varying amplitude, time synchronized signals on the four common and thirty-two segment lines to address the segments to be either "on" or "off."

Figure 8A:
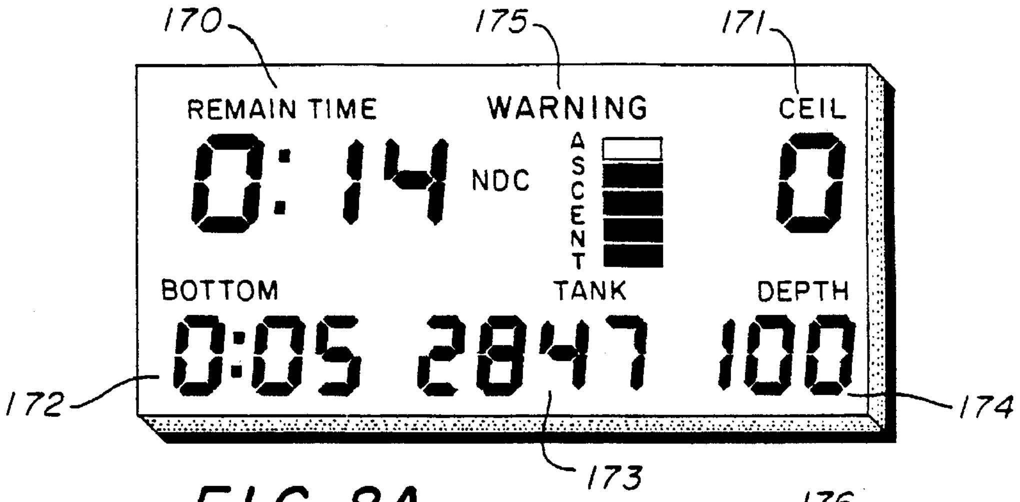
FIGS. 8A and 8B illustrate typical dive parameter information displayed on a normal screen and an alternate screen as controlled by the user of the display unit.
Figure 8B:
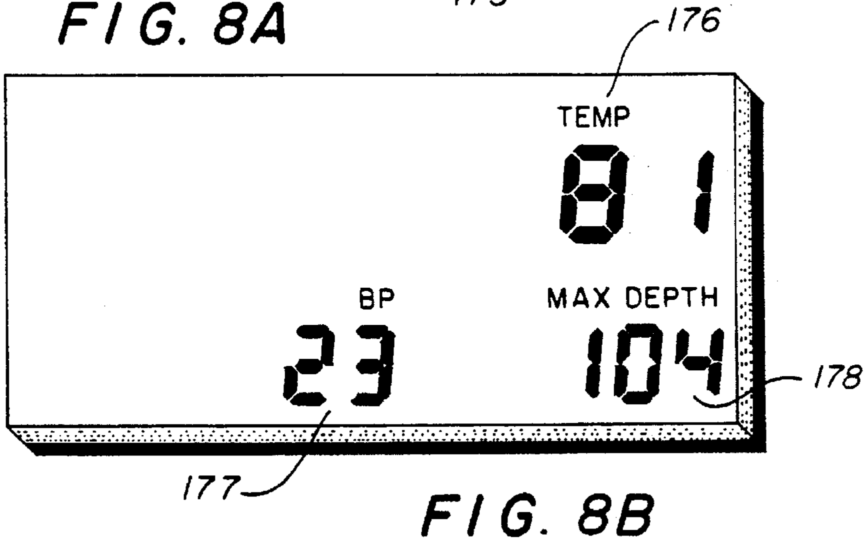

In the preferred form, the information displayed by the display unit can be switched between a normal screen and an alternate screen. FIGS. 8A and 8B illustrate the information capable of being displayed on the dive computer display unit 25. FIG. 8A illustrates the normal screen of display unit 25 when the dive computer is submerged. In this mode the display unit 25 displays air-time remaining 170, ceiling 171, bottom time 172, tank pressure 173, depth 174 and an ascent rate bar graph 175.

Air-time remaining 170 is a prediction of the time it will take the user to use the air remaining in compressed-air tank 13 at the user's current breathing rate.

Ceiling 171 is the depth to which the user may ascend before completing a decompression stop. In the preferred form, ceiling depths are given in ten foot increments from 0 to 30 feet. When programmed to display depth in meters, ceiling depth are shown in increments of 3 meters from 0 to 9 meters. When the user is making a non-decompression dive, the ceiling 171 will read 0, indicating that the user may safely make a direct ascent to the surface without completing any decompression stops. Bottom time 172 begins to count when the user has descended below five feet in the preferred form, and continues to be counted until the user has ascended above three feet.

Tank pressure 173 is the air pressure in compressed-air tank 13. In the preferred form, tank pressure is displayed in increments of 1 psi (or 0.1 bar or 0.1 $kg/cm^2$ in metric units). In the preferred form, if the air pressure drops below 500 psi or below 5 minutes of air-time remaining, the dive computer sounds an audible warning, displays a warning legend on the display unit, and causes the warning legend and tank pressure 173 digits to flash.

Depth 174 is the depth of the user. As noted above, when the tank unit is submerged, it automatically calibrates its depth measurement for either fresh water or sea water and computes the user's actual depth based on the measured ambient pressure. In the preferred form the range displayed is from 0 to 250 feet in increments of 1 foot. When depth is displayed in meters, its range is from 0 to 76 meters in increments of 1 meter.

The ascent rate bar graph 175 allows the user to monitor the rate of ascent. In the preferred form, each bar represents an ascent rate of an additional ten feet per minute with a maximum ascent rate of 60 feet per minute allowed. For example, an ascent rate of 35 feet per minute will cause the ascent bar graph 175 to display three bars, while an ascent rate of 60 feet per minute will cause the ascent bar graph 175 to display all five bars. An ascent rate slower than ten feet per minute will not cause the ascent bar graph 175 to be illuminated.

FIG. 8B illustrates the alternate screen of display unit 25 when the dive computer is submerged. In this mode the display unit 25 displays temperature 176, breathing parameter 177 and maximum depth 178. Temperature 176 is the ambient temperature of the water. Breathing parameter 177 is the indicator of the user's breathing efficiency discussed in detail above. And maximum depth 178 is the maximum depth that the user has descended to on that dive. In the preferred form each dive parameter is updated once every second.

In the preferred form, the user can switch from the normal screen to the alternate screen by depressing the on/off button on the display unit 25. Information on the alternate screen is displayed on LCD 55 for a short period of time, before the display automatically switches back to the normal screen. However, if the user holds the on/off button down, the LCD 55 will continue to display the alternate screen. Thus, in the preferred form the user can control when the alternate screen is displayed and the length of time it is displayed.

The display also includes a warning indicator to alert the user whenever certain dive parameters reach dangerous levels. For example, if the air pressure in the user's compressed-air tank drops below 500 psi the display will cause a WARNING legend and the air pressure indicator to flash. This warning will continue until the tank unit is attached to a compressed-air tank with more than 600 psi or the user surfaces. Similarly, if the user's breathing parameter goes to either zero or ninety-nine, the display will cause the WARNING legend and the diver's breathing parameter to flash and continue flashing until the diver's breathing parameter returns to acceptable levels.

Low Battery Detect Circuit 180

The display unit also includes a low battery detect device 180 to warn the diver whenever the batteries in the display unit are below a certain voltage. In the preferred form, low battery detect circuit 180 consists of a SCI17701Y available from S-MOS, which transmits a signal to microcomputer 60.

The Display Unit On-Off Switch 80

The display unit may either include a "tap-on" on-off switch or a push-button magnetic on-off switch for turning the display unit on and off, both of which eliminate the need for a sealed penetration of the case.

As described in detail for the tank unit, the "tap-on" on switch is activated by the user tapping on the area marked on the outside of the case. On the inside of the case, a piezoelectric element is mounted to the case opposite the marked area for the switch. When the user taps the marked area, the piezoelectric element senses the vibration and generates a signal that is monitored by the display unit microcomputer 60. Once the display unit determines that it has been turned on the LCD 55 is initialized and the display unit begins displaying dive parameter data as it receives it from the tank unit.

Figure 9:
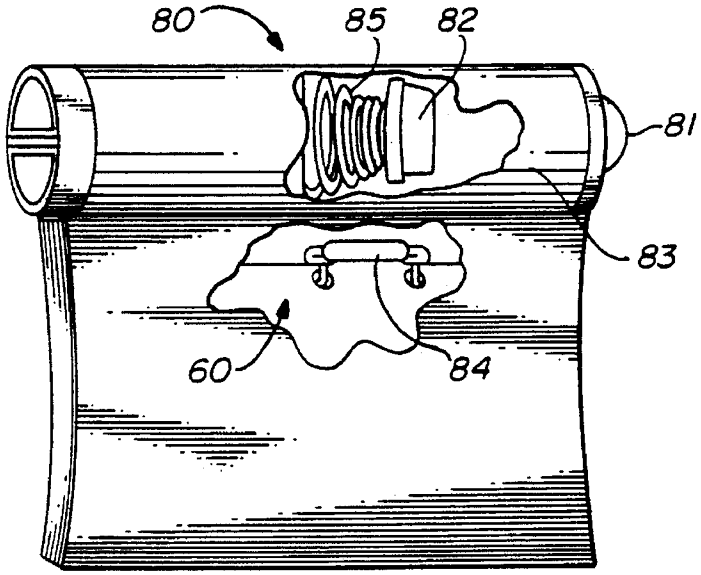
FIG. 9 is a diagram of the on/off switch used to turn the display unit of the dive computer on and off.

The display unit may alternatively include a push-button magnetic on-off switch 80, which is shown in FIG. 9. Push-button 81 is positioned so that when it is depressed it causes ceramic magnet 82 to move along cylinder 83 until it is close enough to reed-switch 84 that the static magnetic field of the magnet actives reed-switch 84. Activation of reed switch 84 is detected by microcomputer 60, which causes the display unit to initialize LCD 55 and begin displaying dive parameter data as it receives it from the tank unit. When the user releases push-button 81, spring 85 returns ceramic magnet 82 to its non-depressed position.

The display unit can be turned off by user depressing push-button 81 and holding it in a depressed position for a approximately two seconds Detailed Description of Data Probe 150

FIG. 10 illustrates tank unit 20 connected to personal computer 200 through data probe 150. As noted above, the data probe 150 can be both mechanically and electrically attached to the tank unit by the same three metal clasps, 21 through 23, that are used to attach the tank unit to the user's low pressure hose 24, and can be connected to personal computer 200 through a standard RS-232 port. Metal clasps 21 through 23 of tank unit 20 attach to metal rings 202 through 204 of data probe 150 and RS-232 connector 201 of data probe 150 attaches to the standard RS-232 port of personal computer 200. The active circuit elements of data probe 150 are physically contained in the data probe RS-232 connector 201.

FIG. 11 is an electrical schematic of the data probe 150 illustrated in FIG. 10. When the tank unit is attached to personal computer 200 through the data probe 150, control and data signals can be transmitted to the tank unit 20 through metal ring 202 and received from the tank unit through metal ring 204. Metal ring 203 is connected to ground. Metal rings 202 and 204 are connected to an RS-232 transceiver 205 through inverters 206 and 207. The principal function of RS-232 transceiver 205 is to convert data acceptable to the dive computer, which is between ground and +5 volts, to data acceptable to an RS-232 port of a personal computer, which is between −12 and +12 volts. In the preferred form, RS-232 transceiver 205 is a MAX231 available from Maxim.

The data probe RS-232 connector 201 is a twenty-five pin connector of which only five pins are used by the data probe. The data terminal ready (DTR) pin 208, receive data (RCV) pin 209 and ready to send (RTS) pin 211 are used to supply power to the active element of the data probe through three pair of diodes 213, 214 and 215. These connections provide +12 volts and −12 volts to RS-232 transceiver 205 and +5 volts to RS-232 transceiver 205 and inverters 206 and 207 through +5 volt regulator 215, which converts +12 volts to +5 volts. In the preferred form, +5 volt regulator 913 is a 78L05 available from either TI or Motorola. Pin 212 is connected to ground.

In addition to providing power to the active elements of the data probe, the receive data pin 209 is also used to transmit serial data to the tank unit through RS-232 transceiver 205 and metal ring 202. The transmit data (XMIT) pin 210 is used to receive data from the tank unit through RS-232 transceiver 205 and metal ring 204.

In operation, the data probe 150 allows data and control signals to be exchanged between tank unit 20 and personal computer 200. This allows the user to recall dive profiles stored in the tank unit 20 and display those dive profiles on the personal computer. As noted above, the user can also read and modify EAROM 39 data to control the operational parameters of the dive computer.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. A dive computer for use by a user of a self-contained underwater breathing apparatus (SCUBA), the dive computer including:

a first pressure transducer for sensing pressure in a compressed-air tank and generating a first signal representing said sensed tank pressure;

a second pressure transducer for sensing ambient water pressure and generating a second signal representing said sensed ambient pressure;

first and second conductors on said dive computer that are exposed to said water;

a microcomputer coupled to said conductors for producing a voltage at said first conductor and determining if said water is fresh water or sea water by measuring the resulting voltage at said second conductor;

said microcomputer operatively coupled to the first pressure transducer and the second pressure transducer for calculating the normalized rate at which air pressure in the compressed-air tank is decreasing normalized for water depth that is adjusted according to the presence of fresh water or sea water; and a display operatively coupled to the microcomputer for displaying information to the user, including at least the normalized rate.

2. The dive computer of claim 1, wherein the display also displays the air pressure in the compressed-air tank and the depth of the user.

3. The dive computer of claim 1, wherein the first pressure transducer is contained within a tank unit, and the display is contained within a display unit that is physically separate from the tank unit.

4. The dive computer of claim 3, wherein the tank unit includes a transmitter coupled to the first pressure transducer for transmitting a modulated signal indicative of at least the air pressure in the compressed-air tank and the display unit includes a receiver coupled to the display for receiving the modulated signal transmitted by the transmitter.

5. The dive computer of claim 4, wherein the display also displays the air pressure in the compressed-air tank and the depth of the user.

6. The dive computer of claim 1, wherein the first pressure transducer, the second pressure transducer and the microcomputer are contained within a tank unit, and the display is contained within a display unit that is physically separate from the tank unit.

7. The dive computer of claim 6, wherein the tank unit includes a transmitter coupled to the microcomputer for transmitting a modulated signal indicative of at least the air pressure in the compressed-air tank and the display unit includes a receiver coupled to the display for receiving the modulated signal transmitted by the transmitter.

8. The dive computer of claim 7, wherein the display unit includes a second microcomputer and the receiver is coupled to the display through the second microcomputer.

9. The dive computer of claim 1, including:

an analog to digital converter coupled to the first pressure transducer and the second pressure transducer for digitally encoding said first and second signals representing said tank pressure and said sensed ambient pressure; and said digitally encoded signals being coupled to the microcomputer.

10. The dive computer of claim 1, wherein the microcomputer includes a memory for storing for later retrieval the rate at which air pressure in the compressed-air tank is decreasing normalized for depth.

11. The dive computer of claim 1, wherein the dive computer includes an audible alarm circuit coupled to the microcomputer for sounding an alarm when the rate at which air pressure in the compressed-air tank is decreasing normalized for depth goes beyond a certain level.

12. A dive computer for use by a user of a self-contained underwater breathing apparatus (SCUBA), the dive computer including:

a tank unit attached to said apparatus for electrically measuring various dive parameters;

a first pressure transducer in said tank unit for sensing pressure in a compressed-air tank;

a "tap on" switch sealed inside said tank unit for electrically energizing said tank unit by responding to the user tapping on a predetermined area on said tank unit;

a second pressure transducer for sensing ambient water pressure;

a normally-off microcomputer operatively coupled to the first pressure transducer and the second pressure transducer;

enabling means coupled to said microcomputer for energizing said microcomputer for calculating the user's breathing parameter, which is indicative of the rate at which air pressure in the compressed-air tank is decreasing normalized for the depth; and a display operatively coupled to the microcomputer for displaying information to the user, including at least the user's breathing parameter.

13. The dive computer of claim 12, wherein the display is contained within a display unit that is physically separate from the tank unit containing the first pressure transducer.

14. The dive computer of claim 13, wherein the tank unit includes a transmitter coupled to the first pressure transducer for transmitting a modulated signal indicative of at least the air pressure in the compressed-air tank and the display unit includes a receiver coupled to the display for receiving the modulated signal transmitted by the transmitter.

15. The dive computer of claim 14, wherein the display also displays the air pressure in the compressed-air tank and the depth of the user.

16. The dive computer of claim 12, wherein the microcomputer includes a memory for storing the user's breathing parameter for later retrieval.

17. The dive computer of claim 12, wherein the dive computer includes an audible alarm circuit coupled to the microcomputer for sounding an alarm when the user's breathing parameter goes beyond predetermined limity.

18. A method of monitoring a diver's breathing parameter, including the steps of:

measuring air pressure in a compressed-air tank;

measuring ambient water pressure;

measuring the salinity of the water;

calculating the depth of the diver based on the measured salinity of the water;

calculating, at predetermined time intervals, the rate at which air pressure in the compressed-air tank is decreasing;

calculating the diver's breathing parameter by dividing the calculated rate at which air pressure in the compressed-air tank is decreasing by the calculated depth of the diver; and displaying the diver's breathing parameter.

19. The method of claim 18, including the step of storing the diver's breathing parameter in memory for later retrieval so that the breathing efficiency of the diver can be tracked from dive-to-dive.

20. An electronic device, for use by a user of a self-contained breathing apparatus, the electronic device including:

a first pressure transducer for sensing the pressure in a compressed-air tank;

a second pressure transducer for sensing ambient water pressure;

a water salinity detector;

a microcomputer operatively coupled to the first pressure transducer, the second pressure transducer, and the water salinity detector for calculating the user's breathing parameter, which is indicative of the rate at which the air pressure in the compressed-air tank is decreasing normalized for user depth; and a display operatively coupled to the microcomputer for displaying information to the user, including at least the user's breathing parameter.

21. The electronic device of claim 20, wherein the first pressure transducer is contained within a tank unit, and the display is contained within a display unit that is physically separate from the tank unit.

22. The electronic device of claim 21, wherein the tank unit includes a transmitter coupled to the first pressure transducer for transmitting a modulated signal indicative of at least the air pressure in the compressed-air tank and the display unit includes a receiver coupled to the display for receiving the modulated signal transmitted by the transmitter.

23. The dive computer of claim 22, wherein the display also displays the air pressure in the compressed-air tank and the depth of the user.

24. The dive computer of claim 20, wherein the first pressure transducer, the second pressure transducer and the microcomputer are contained within a tank unit, and the display is contained within a display unit that is physically separate from the tank unit.

25. The dive computer of claim 20, wherein the microcomputer includes a memory for storing the normalized rate at which air pressure in the compressed-air tank is decreasing for later retrieval.

26. A dive computer for use by a user of a self-contained underwater breathing apparatus (SCUBA), the dive computer including:

a tank unit for transmitting information and a display unit for receiving the information transmitted by the tank unit and displaying at least a portion of that information to the user, the tank unit being physically separate from said display unit and including:

a water salinity sensor;

a first pressure transducer for sensing air pressure in a compressed-air tank;

a second pressure transducer for sensing ambient water pressure;

a microcomputer coupled to the first pressure transducer, the second pressure transducer, and the salinity sensor for calculating the user's breathing parameter, which is indicative of the rate at which air pressure in the compressed air tank is decreasing normalized with respect to both the user's depth and water salinity; and a transmitter coupled to the microcomputer for transmitting a modulated signal indicative of at least the user's breathing parameter;

the display unit including:

a receiver for receiving the modulated signal transmitted by the tank unit; and a display coupled to the receiver for displaying information to the user, including at least the user's breathing parameter.

27. The dive computer of claim 26, wherein the microcomputer includes a memory for storing the user's breathing parameter for later retrieval.

28. A dive computer for use by a user of a self-contained underwater breathing apparatus (SCUBA), the dive computer including:

a first pressure transducer for sensing pressure in a compressed-air tank and periodically generating an analog signal indicative of the air pressure in the tank;

a second pressure transducer for sensing ambient water pressure and periodically generating an analog signal indicative of ambient water pressure;

an analog to digital converter coupled to the first pressure transducer and the second pressure transducer for converting the analog tank pressure signal and the analog ambient water pressure signal into digital signals;

a water salinity detector for generating a signal indicating fresh water or sea water;

a microcomputer coupled to the analog to digital converter and said water salinity detector for calculating user depth and the rate at which air pressure in the compressed-air tank is decreasing normalized for said calculated user depth, said calculated user depth being adjusted by said microcomputer according to the presence of fresh water or sea water; and a display coupled to the microcomputer for displaying information to the user, including the normalized rate at which air pressure in the compressed-air tank is decreasing.

29. The dive computer of claim 28, wherein the display also displays the air pressure in the compressed-air tank and the depth of the user.

30. The dive computer of claim 28, wherein the first pressure transducer is contained within a tank unit, and the display is contained within a display unit that is physically separate from the tank unit.

31. The dive computer of claim 30, wherein the tank unit includes a transmitter coupled to the microcomputer for transmitting a modulated signal indicative of at least the air pressure in the compressed-air tank and the display unit includes a receiver coupled to the display for receiving the modulated signal transmitted by the transmitter.

32. The dive computer of claim 28, wherein the microcomputer includes a memory for storing the normalized rate at which air pressure in the compressed-air tank is decreasing for later retrieval.

33. The dive computer of claim 28, wherein the dive computer includes an alarm circuit coupled to the microcomputer for sounding an audible alarm when the user's breathing parameter is above a certain level.

34. The dive computer of claim 28, wherein the dive computer includes an alarm circuit coupled to the microcomputer for sounding an audible alarm when the user's breathing parameter is below a certain level.

* * * * *